(12) United States Patent
Gerson et al.

(10) Patent No.: US 6,465,448 B1
(45) Date of Patent: Oct. 15, 2002

(54) METHOXYAMINE POTENTIATION OF TEMOZOLOMIDE ANTI-CANCER ACTIVITY

(75) Inventors: Stanton L. Gerson, Pepper Pike; Lili Liu, Euclid, both of OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 09/373,693

(22) Filed: Aug. 13, 1999

(51) Int. Cl.$^7$ .......................... A61K 31/33; A61K 31/13

(52) U.S. Cl. ..................................... 514/183; 514/645
(58) Field of Search ........................... 514/183; 574/645

(56) References Cited

U.S. PATENT DOCUMENTS 5,731,304 A    3/1998   Baer et al. ................... 514/183

FOREIGN PATENT DOCUMENTS

JP        10045589    *  2/1998   ................. 514/183
WO        WO 94/15615    7/1994

OTHER PUBLICATIONS

Thomale et al., Haematol. Blood Transfus., 39, pp 3–12 Abstract Only, 1998.*

Liu et al., Clin. Cancer Res., 5(10), pp 2908–2917 Abstract Only, 1999.*

Mitchell and Dolan, "Effect of temozolomide and dacarbazine on $O^6$alkylguanine–DNA alkyltransferase activity and sensitivity of human tumor cells and xenografts to 1,3–bis(2–chloroethyl)–1–nitrosourea," *Cancer Chemother Pharmacol* 32:59–63 (1993).

Pegg et al., "Structure, function and inhibition of $O^6$–alkylguanine–DNA AGT," *Prog. Nucleic Acid Res. Mol. Biol.* 51:167–233 (1995).

Fink et al., "The role of DNA mismatch repair in drug resistance," *Clin. Cancer Res.* 4:1–6 (1998).

Branch et al., "Defective mismatch binding and a mutator phenotype in cells tolerant to DNA damage," *Nature* 362:652–654 (1993).

Kat et al., "An alkylation–tolerant, mutator human cell line is deficient in strand–specific mismatch repair," *Proc. Natl. Acad. Sci. USA* 90:6424–6428 (1993).

Karran and Bignami, "DNA damage tolerance, mismatch repair and genome instability," *BioEssays* 16:833–839 (1994).

Griffin et al., "DNA mismatch binding and incision at modified guanine bases by extracts of mammalian cells: implications for tolerance to DNA methylation damage," *Biochemistry* 33:4787–4793 (1994).

Liu et al., "Mismatch repair mutations override alkyltransferase in conferring resistance to temozolomide by not to 1,3–bis(2–chloroethyl)nitrosourea," *Cancer Res.* 56:5375–5379 (1996).

O'Connor et al., "Isolation and structure of a cDNA expressing a mammalian 3–methyladenine–DNA glycosylase," *EMBO J.* 9:3337–3342 (1990).

Samson et al., "Cloning and characterization of a 3–methyladenine DNA glycosylase cDNA from human cells whose gene maps to chromosome 16," *Proc. Natl. Acad. Sci. USA* 88:9127–9131 (1991).

Neddermann et al., "Cloning and Expression of Human G/T Mismatch–specific Thymine–DNA Glycosylase," *J. Biol. Chem.* 271:12767–12774 (1996).

Vollberg et al., "Isolation and characterization of the human uracil DNA glycosylase gene," *Proc. Natl. Acad. Sci. USA* 86: 8693–8697 (1989).

Olsen et al., "Molecular cloning of human uracil–DNA glycosylase, a highly conserved DNA repair enzyme," *EMBO J.* 8:3121–3125 (1989).

Radicella et al., "Cloning and characterization of hOOG1, a human homolog of the OGG1 gene of *Saccharomyces cerevisiae*," *Proc. Natl. Acad. Sci. USA* 94:8010–8015 (1997).

Rosenquist et al., "Cloning and characterization of a mammalian 8–oxoguanine DNA glycosylase," *Proc. Natl. Acad. Sci. USA* 94:7429–7434 (1997).

Wilson, "Mammalian base excision repair and DNA polymerase beta," *Mutation Res.* 407:203–215 (1998).

Molinete et al., "Over production of the poly (ADP–ribose) polymerase DNA–binding domain blocks alkylation–induced DNA repair synthesis in mammalian cells," *EMBO J.* 12:2109–2117 (1993).

Caldecott et al., "XRCC1 polypeptide interacts with DNA polymerase $\beta$ and possibly poly (ADP–ribose) polymerase, and DNA ligase III is a novel molecular 'nick–sensor' in vitro," *Nucleic Acids Res.* 24:4387–4394 (1996).

Sobol et al., "Requirement of mammalian DNA polymerase–$\beta$ in base–excision repair," *Nature* 379:183–186 (1996).

Walker et al., "A role for the human DNA repair enzyme HAP1 in cellular protection against DNA damaging agents and hypoxic stress," *Nucleic Acids Res* 22:4884–4889 (1994).

Engelward et al., "Repair–deficient 3–methyladenine DNA glycosylase homozygous mutant mouse cells have increased sensitivity to alkylation–induced chromosome damage and cell killing," *EMBO* 15:945–952 (1996).

(List continued on next page.)

Primary Examiner—Jerome D. Goldberg
(74) Attorney, Agent, or Firm—Medlen & Carroll, LLP

(57) ABSTRACT

This invention generally relates to novel compositions and methods for the treatment of certain cancers. Additionally, this invention relates to novel compositions and methods to screen drugs for the treatment of certain cancers. Specifically, the invention contemplates that temozolomide and methoxyamine, in combination or in sequence, shall be used as a treatment for certain tumors that are resistant to treatment by temozolomide alone.

21 Claims, 12 Drawing Sheets-

OTHER PUBLICATIONS

Coquerelle et al., "Overexpression of N–methylpurine–DNA glycosylase in Chinese hamster ovary cells renders them more sensitive to the production of chromosomal aberrations by methylating agents– a case of imbalanced DNA repair," *Mutation Res.* 336:9–17 (1995).

Menissier–de Murcia et al., "Requirement of poly (ADP—ribose) polymerase in recovery from DNA damage in mice and in cells," *Proc. Natl. Acad. Sci. USA* 94:7303–7304 (1997).

Boulton et al., "Potentiation of temozolomide–induced cytotoxicity: a comparative study of the biological effects of poly (ADP–ribose) polymerase inhibitors," *Br. J. Cancer,* 72:849–856 (1995).

Fortini et al., "Mutagenic processing of ethylation damage in mammalian cells: the use of methoxyamine to study apurinic/apyrimidinic site–induced mutagenesis," *Cancer Res.* 53:1149–1155 (1993).

Liuzzi and Talpeart–Borle, "A new approach to the study of the base–excision repair pathway using methoxyamine," *J. Biol. Chem.* 260:5252–5258 (1985).

Rosa et al., "Processing in vitro of an abasic site reacted with methoxyamine: a new assay for the detection of abasic sites formed in vivo," *Nucleic Acids Res.* 19: 5569–5574 (1991).

Fortini et al., "Methoxyamine modification of abasic sites protects CHO cells from the cytotoxic and mutagenic effects of oxygen alkylation," *Carcinogenesis* 13: 87–93 (1992).

Kingma and Osheroff, "Apurinic sites are position–specific topoisomerase II poisons," *J. Biol. Chem.* 272: 1148–1155 (1997).

Robertson et al., "Down–regulation of apurinic/apyrimidinic endonuclease expression is associated with the induction of apoptosis in differentiating myeloid leukemia cells," *Cell Growth & Differentiation* 8: 443–449 (1997).

Buschfort et al., "DNA excision repair profiles of normal and leukemic human lymphocytes: functional analysis at the single–cell level," *Cancer Res.* 57: 651–658 (1997).

Wedge et al., "3–Aminobenzamide and /or $O^6$benzylguanine evaluated as an adjuvant to temozolomide or BCNU treatment in cell lines of variable mismatch repair status and $O^6$–alkylguanine–DNA alkyltransferase activity," *Br. J. Cancer* 74: 1030–1036 (1996).

Wilson et al., "Life without DNA repair," *Proc. Natl. Acad. Sci. USA* 94: 12754–12757 (1997).

Gonzaga et al., "Identification of the cross–link between human $O^6$–methylguanine–DNA methyltransferase and chloroethylnitrosourea–treated DNA," *Cancer Res.* 52:6052–6058 (1992).

Prakash and Gibson, "Sequence–selective depurination, DNA interstrand cross–linking and DNA strand break formation associated with alkylated DNA," *Carcinogenesis* 13: 425–431 (1992).

Malapetsa et al.,"Identification of a 116 kDa protein able to bind 1,3–bis (2–chloroethyl)–1–nitrosourea–damaged DNA as poly (ADP–ribose) polymerase," *Mutation Res.* 362: 41–50 (1996).

Matijasevic et al., "Protection against chloroethylnitrosourea cytotoxicity by eukaryotic 3–methyladenine DNA glycosylase" *Proc. Natl. Acad. Sci. USA,* 90:11855–11859 (1993).

Kaina et al., "Chromosomal instability, reproductive cell death and apoptosis induced by $O^6$–methylguanine in Mex–, Mex+ and methylation–tolerant mismatch repair compromised cells: facts and models," *Mutation Res.* 381: 227–241 (1997).

Lindahl et al., "Post–translational modification of poly(ADP–ribose) polymerase induced by DNA strand breaks," *Trends Biochem Sci* 20:405–411 (1995).

Lazebnik et al., "Cleavage of poly(ADP–ribose) polymerase by a proteinase with properties like ICE," *Nature* 371: 346–347 (1994).

Morris et al., "Flow cytometric evaluation of cell–cycle progression in ethyl methanesulfonate and methyl methanesulfonate–exposed P3 cells: relationship to the induction of sister–chromatid exchanges and cellular toxicity," *Environ. Mol. Mutagen.* 18: 139–149 (1991).

Chou and Talalay, "Quantitative analysis of dose–effect relationship: the combined effects of multiple drugs on enzyme inhibitors," In: G. Weber (ed.) *Advances in Enzyme Regulation,* pp. 27–55, New York: Pergamon Press, 1983.

Choy et al., "Concurrent PPaclitaxel, Carboplatin, and Radiation Therapy for Locally Advanced Non–Small Cell Lung Cancer," *Seminars in Onology,* vol. 26(1) Suppl 2:36–43 (1999).

Claij et al., "Microsatellite Instability in Human Cancer: A Prognostic Marker fro Chemotherapy?," *Exper Cell Res* 246:1–10 (1999).

Gunderson, "Indications for and Results of Combined Modality Treatment of Colorectal Cancer," *Acta Oncologica* 38:7–21 (1999).

Hainsworth et al., "The Current Role and Future Prospects of Paclitaxel in the Treatment of Small Cell Lung Cancer," *Seminars in Onology,* vol. 26(1) Suppl 2:60–66 (1999).

Midgley et al., "Colorectal cancer," *Lancet* 353:391–99 (1999).

Neijt et al., "Paclitaxel/Carboplatin for the Initial Treatment of Advanced Ovarian Cancer," *Seminars in Onology,* vol. 26(1) Suppl 2:78–83 (1999).

Pera et al., "Exceptional sensitivity of testicular germ cell tumour cell lines to the new anti–cancer agent, temozolomide," *Br J Cancer* 71(5):904–6 (1995).

Perez, "Paclitaxel Plus Nonanthracycline Combinations in Metastatic Breast Cancer," *Seminars in Onology,* vol. 26(1) Suppl 2:21–26 (1999).

Tentori et al., "Role of Wild–Type p53 on the Antineoplastic Activity of Temozolomide Alone or Combined with Inhibitors of Poly(ADP–Ribose) Polymerase," *J Pharmacol Exp Ther* 285:884–93 (1998).

Von Hoff, "Promising New Agents for Treatment of Patients With Colorectal Cancer," *Seminars in Onology,* vol. 25(5) Suppl 11:47–52 (1998).

Kerr et al., "Novel therapeutic strategies for colorectal cancer," *Hosp Med* 59:617–21 (1998).

Ahnen, "Colon Cancer Prevention by NSAIDs: What is the Mechanism of Action?," *Eur J Surg* 582:111–114 (1998).

Wedge et al., "In vitro evalution of temozolomide combined with X–irradiation," *Anti–Cancer Drugs* 8:92–97 (1997).

Link et al., "Basic research supported developments of chemotherapy in nonresectaable isolated colorectal liver metastases to a protocol of hepatic artery infusion using mitoxantrone, 5–FU + folinic acid and mitomycin C," *Gan To Kagaku Ryoho* 26:269–81 (1999) [abstract only].

Wedge et al., "Effect of Single and Multiple Administration of an O6–benzylguanine/temozolomide Combination: an Evaluation in a Human Melenoma Xenograft Model," *Cancer Chemother Pharmacol* 40:266–272 (1997).

Bianchi et al., "O6–methylguanine–DNA Methyltransferase Activity and Induction of Novel Immunogenicity in Murine Tumor Cells Treated with Methyhylating Agents," *Cancer Chemother Pharmacol* 29:277–282 (1992).

\* cited by examiner

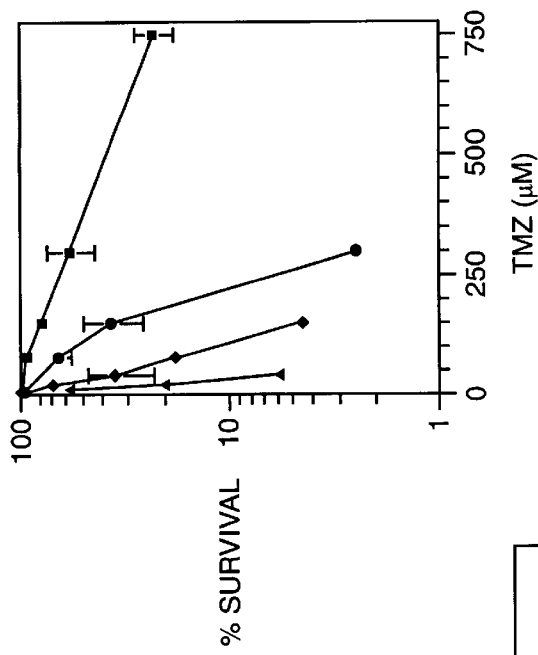
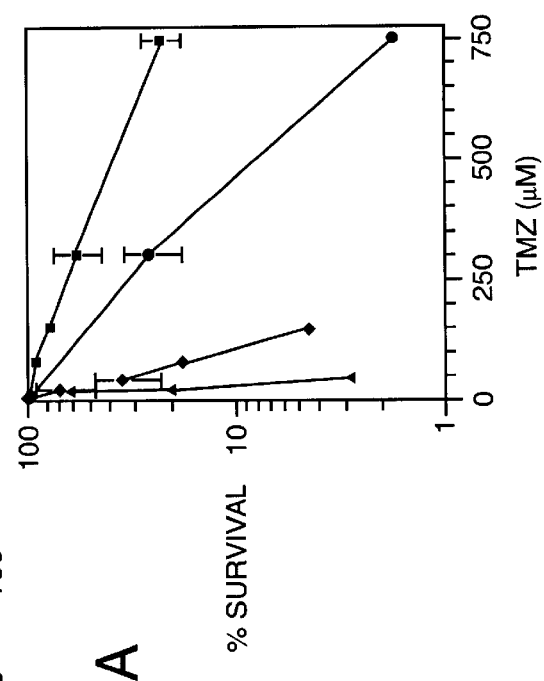
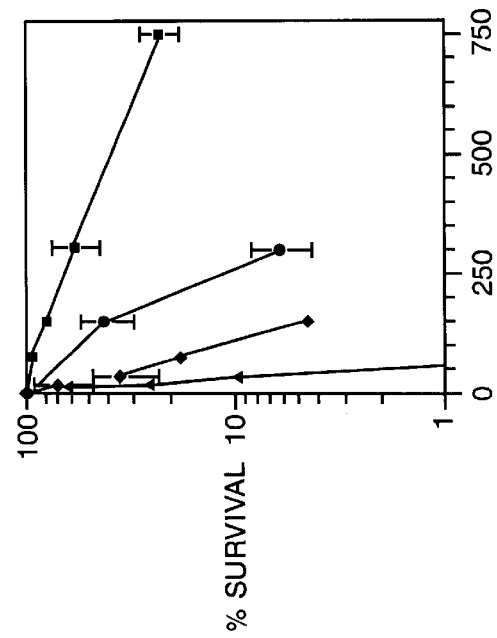
FIG. 3A
FIG. 3B
FIG. 3C

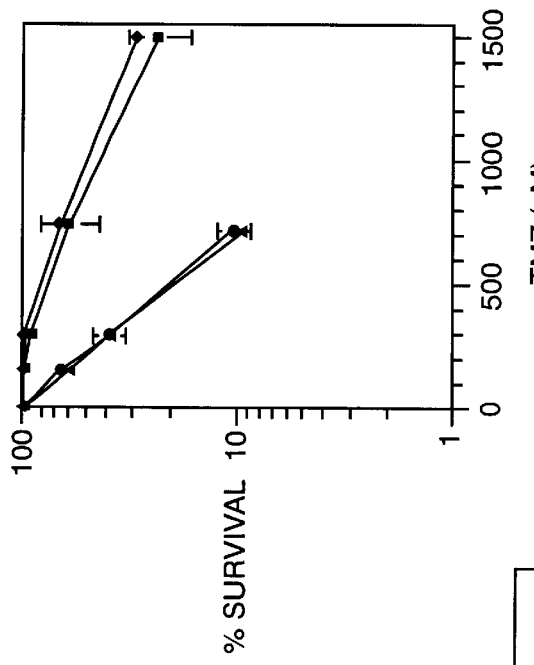
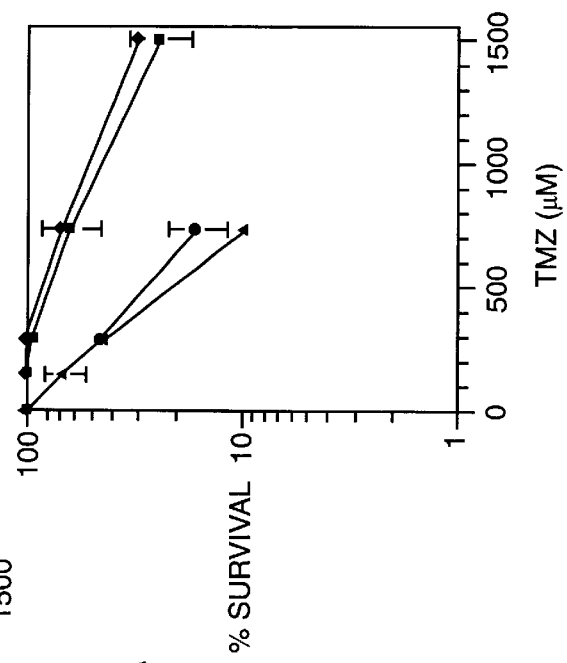
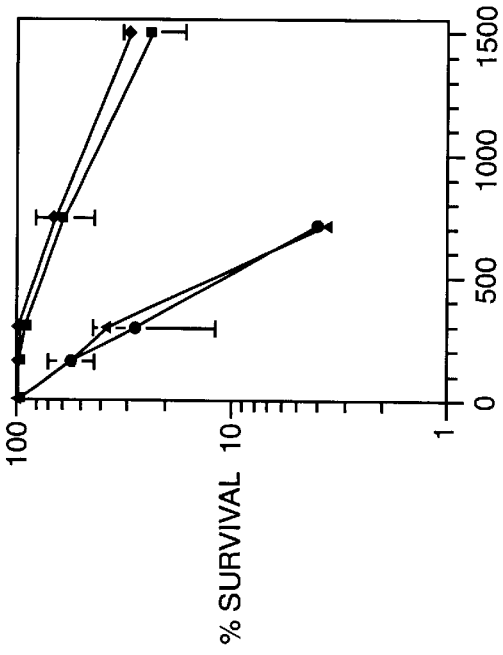
FIG. 4A
FIG. 4B
FIG. 4C

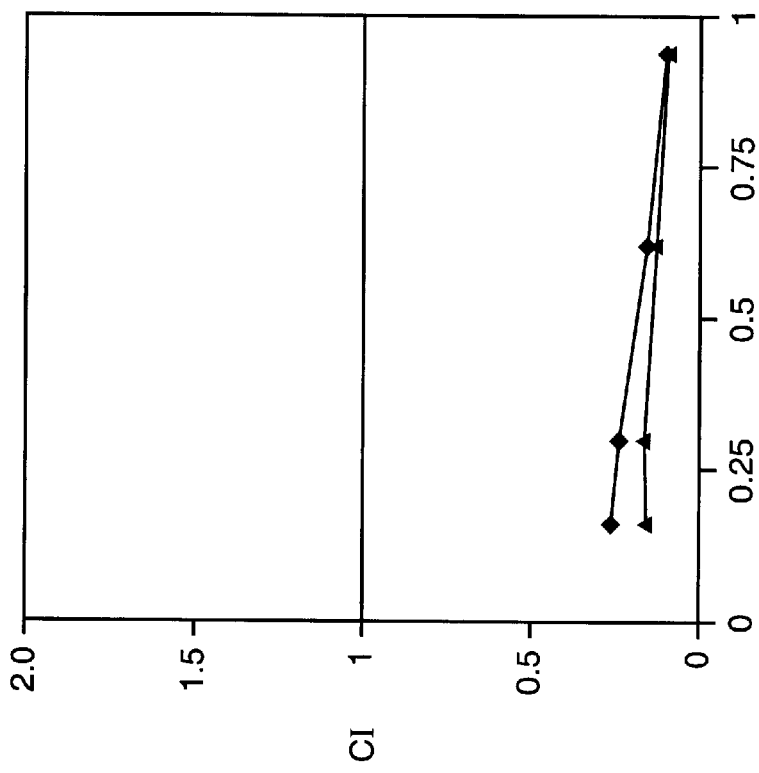
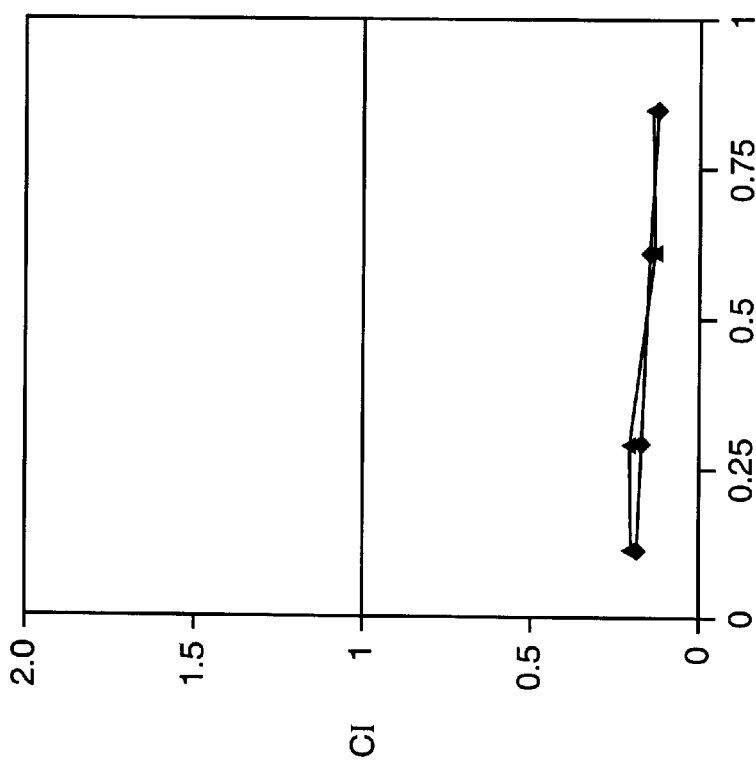
FIG. 5B
FIG. 5A

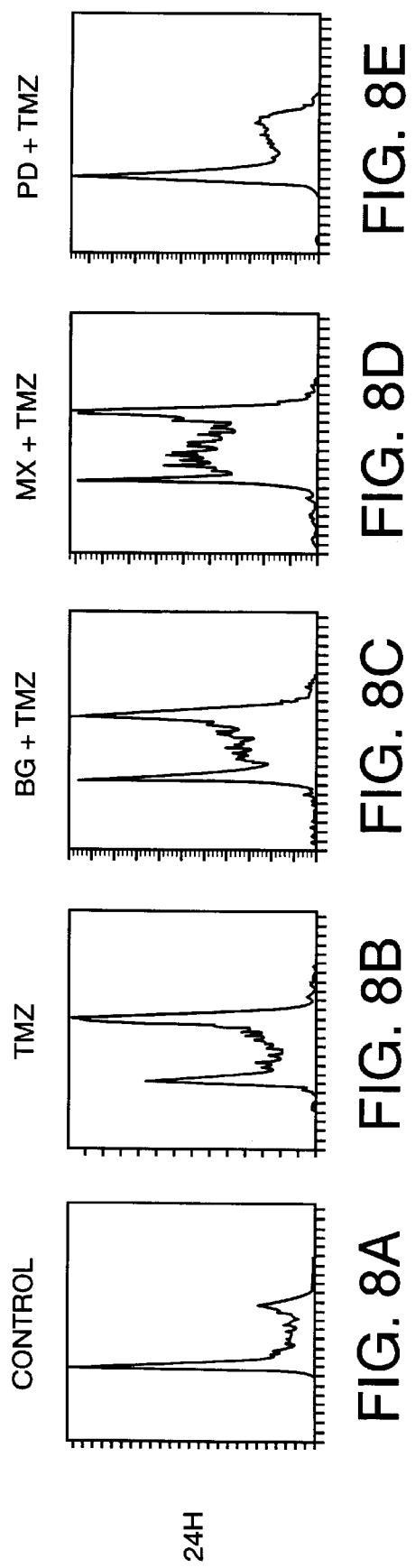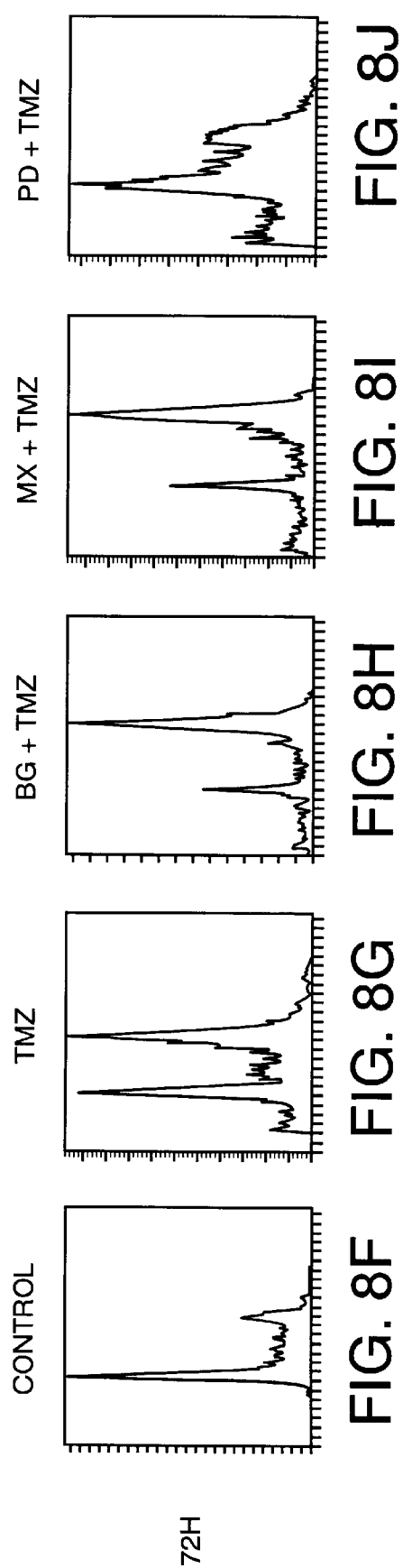

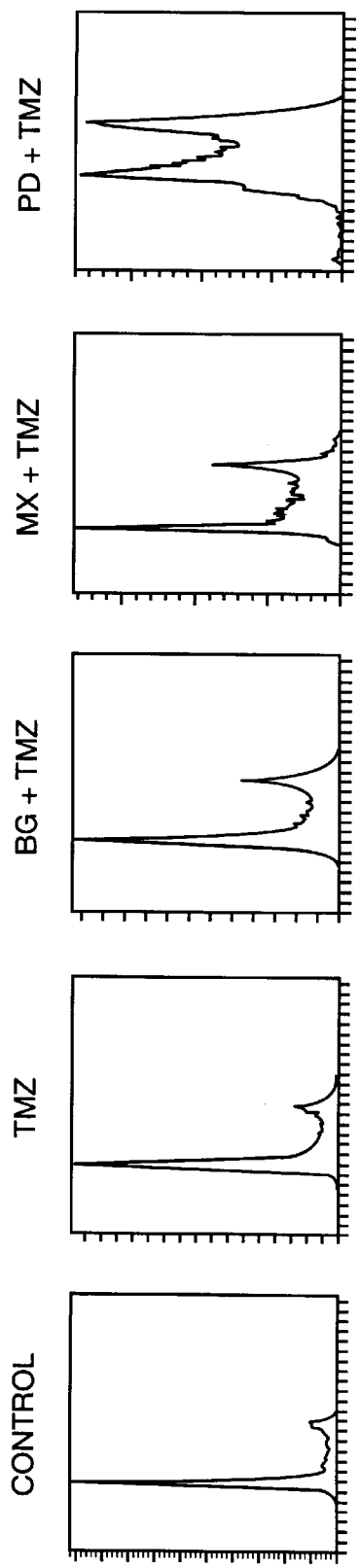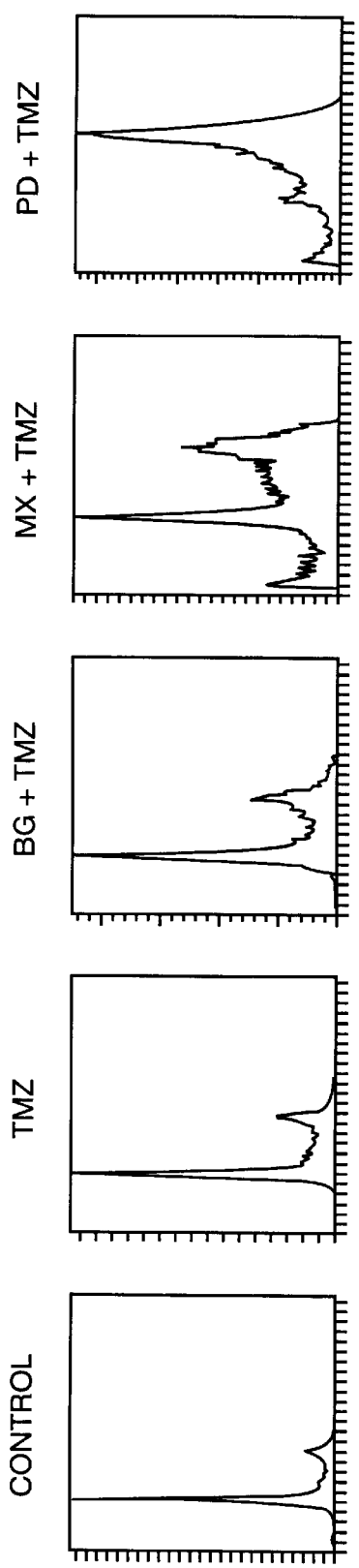

METHOXYAMINE POTENTIATION OF TEMOZOLOMIDE ANTI-CANCER ACTIVITY

This invention was made in part with government support under grants RO1CA73062, RO1ES06288, UO1CA75525 and P30CA43703 from the USPHS. The government has certain rights in the invention.

FIELD OF THE INVENTION

This invention generally relates to novel compositions and methods for the treatment of certain cancers. Additionally, this invention relates to novel compositions and methods to screen drugs useful for the treatment of certain cancers.

BACKGROUND

Cancer is a worldwide problem. The American Cancer Society estimates that over one half million people will die from cancer in the United States alone in 1999. As such, finding novel compositions and methods for the treatment of cancer is of vital interest. The treatment of cancer falls into three general categories: chemotherapy, radiation therapy and surgery. Often, therapies are combined since a combination of therapies often increases the probability the cancer will be eradicated as compared to treatment strategies utilizing a single therapy. Most typically, the surgical excision of large tumor masses is followed by chemotherapy and/or radiation therapy.

Chemotherapeutic agents can work in a number of ways. For example, chemotherapeutic can work by interfering with cell cycle progression or by generating DNA strand breaks. If the cancer cell is not able to overcome the cell cycle blockage or cell injury caused by the therapeutic compound, the cell will often die via apoptotic mechanisms. The use of a single chemotherapeutic agent in the treatment of cancer, with or without surgery or radiation, has several disadvantages. First, the cells may develop resistance to the chemotherapeutic agent. Such resistance results either in the requirement for higher dosages of the drug and/or the renewed spread of the cancer. Chemotherapeutic agents can be toxic to the patient. Therefore, there is a practical upper limit to the amount that a patient can receive. However, if two chemotherapeutic agents are used in concert, the dosage of any single drug can be lowered. This is beneficial to the patient since using lower levels of chemotherapeutic agents is generally safer for the patient. Additionally, cancer cells are less likely to generate resistance to the combination of drugs as they are to a single drug.

The design of drug combinations for the chemotherapeutic treatment of cancer should be approached with the goals of 1) finding a combination that is synergistic with and not merely additive to the first compound with respect to the elimination of the tumor, and 2) finding a second drug that does not potentiate the toxic effects of the first chemotherapeutic agent. These conditions require a great deal of empirical testing of agents known to have anticancer properties with agents that either may have anticancer properties, or that may augment the first agent in other ways. TMZ is currently employed in chemotherapeutic treatment of certain tumors. It works by dramatically increasing the mutation rate of cells undergoing DNA replication. Such cells, because of the high number of mutations which they have acquired as a result of the treatment with TMZ, are rapidly removed by apoptosis, thereby potentially eliminating the tumor. Some tumor cells are resistant to treatment by TMZ due to deficiencies in the mismatch repair (MMR) system in the cell. A defective MMR system prevents the cell from recognizing $O^6mG$ DNA adducts thereby making the cell resistant to elimination.

Baer et al., in U.S. Pat. No. 5;731,304, note that the toxicity of temozolomide can be potentiated by agents that inhibit the enzyme $O^6$-alkylguanine DNA alkyltrarisferase (ATase). In particular, they note that $O^6$-benzylguanine (BG) can enhance the toxicity of temozolomide in certain cell lines that exhibit high levels of ATase (e.g. 300-fold in MAWI cells). However, in other cell lines that exhibit lower levels of ATase (e.g. U373 cells) the effect is significantly less.

Mitchell and Dolan (*Cancer Chemother Pharmocol* 32:59–63, 1993) note that temozolomide (TMZ) and an analogue, 5-(dimethyltriazeno)imidazole-4-caroxamide (DITC), can be effective in enhancing the anti-tumor effects of 1,3-bis(2-chloroethyl)-1-nitrosourea (BCNU). TMZ and DITC work by depleting cells or tumors of $O^6$-alkylguanine-DNA alkytransferase (AGT). AGT is a DNA repair protein that selectively removes adducts from the $O^6$ position of guanine in DNA by a stoichiometric transfer of the alkyl group to a cysteine moiety. Removal of the alkyl group from the DNA by methylation of the $O^6$ position of the guanine effectively inactivates the AGT. As with the patent referred to above, the disclosed method is limited to specific cells or cancers.

Therefore, what is need is the development of novel therapies that utilize the synergistic properties of two or more therapeutic agents for the treatment of cancer that have a broader range of targets or a different range of targets than those combination therapies already known.

SUMMARY OF THE INVENTION

The invention contemplates that temozolomide (TMZ) and methoxyamine (MX) shall be used as a treatment for certain tumors that are resistant to treatment by TMZ alone. Additionally, the invention contemplates the TMZ and inhibitors of poly (ADP-ribose polymerase (PARP) shall be used as a treatment for certain tumors that. are resistant to treatment by TMZ alone. The present invention generally comprises novel compositions to 1) screen for compounds that can potentiate or modulate the therapeutic effect of temozolomide (TMZ) alone or combined with methoxyamine (MX), 2) provide model systems for the study of cancer treatments by agents that modulate DNA repair mechanisms and 3) provide treatments for certain cancers.

With regard to the treatment of cancer, the present invention contemplates methods of treating cancer that utilize TMZ in conjunction with another agent that is capable of potentiating the toxic effect of the TMZ. More specifically, the invention relates to potentiating the effect of TMZ with agents that modify DNA adducts created by TMZ. Even more specifically, the invention relates to potentiating the effect of TMZ with agents that modify $N^7$-methylguanine ($N^7mG$) and $N^3$-methyladenine ($N^3mA$) DNA adducts. One example of such an agent is MX. The present invention is not limited by the order in which the agents are administered. In one embodiment, the agents are administered sequentially. In another embodiment, the agents are administered as a combined formulation (i.e., a formulation comprising methoxyamine and temezolomide). In one embodiment, the present invention contemplates a method of treating cancer comprising: a) providing i) a patient diagnosed with cancer, ii), a first formulation comprising methoxyamine and iii) a second formulation comprising temozolomide; b) administering said first formulation to said patient; and c) administering said second formulation to said patient.

Additionally, the invention relates to potentiating temozolomide with agents that interfere with the ability of PARP to be effective in DNA repair by either competing with PARP, inhibiting PARP or degrading PARP. The present invention is not limited to the agent used to inhibit PARP activity. In one embodiment, PD128763 is used. In another embodiment 6-AN is used. In another embodiment, 3-AB is used. The present invention is not limited by the order in which the agents are administered. In one embodiment the agents are administered sequentially. In another embodiment, the agents are administered as a combined formulation. In one embodiment, the present invention contemplates a method of treating cancer comprising: a) providing i) a patient diagnosed with cancer, ii) a first formulation comprising a poly-(ADP-ribose)-polymerase inhibitor and iii) a second formulation comprising temozolomide; b) administering said first formulation to said patient; and c) administering said second formulation to said patient.

The present invention is not limited to the method of administration of the treatment. In one embodiment, the treatment is administered orally. In another embodiment the treatment is administered intravenously. In yet another embodiment, the treatment is administered intraperitoneally. In yet another embodiment, the treatment is administered directly to the tumor by injection or, in the case of skin tumors, for example, by direct application of creams or ointments.

As noted above, the present invention also contemplates screening assays to identify drugs that augment the ability of temozolomide to inhibit tumor growth, drugs that augment the ability of temozolomide with methoxyamine to inhibit tumor growth, and drugs that augment the ability of temozolomide with PARP inhibitors to inhibit tumor growth. A variety of assay formats are contemplated for testing the potential of compounds suspected of augmenting the anti-tumor effect of TMZ. In one embodiment, cells are pretreated with the compound suspected of augmenting the anti-tumor effect of temozolomide, followed by treatment with temozolomide. Cell growth and/or cell death are then measured to determine if there is a an anti-tumor effect. In another embodiment, cells are treated with the compound suspected of augmenting the anti-tumor effect of temozolomide at approximately the same time as they are treated with temozolomide. Cell growth and/or cell death are then measured to determine if the regime had an anti-tumor effect. The invention is not limited to any particular measurement technique for apoptosis or cell growth. Various methods are envisioned. For example, mitosiscan be measured by use of fluorescent dyes that intercalate into DNA, by the measurement of $H^3$-thymidine incorporation or by colorimetric assays. Such assays permit the use of high throughput screening methods. Apoptosis can be measured by the use of fluorescent dyes that intercalate into DNA, annexin-V staining of phosphotidyl serine residues of the cell surface or morphological changes in cell appearance.

The present invention contemplates a method of screening for compounds that augment the anti-tumor effect of temolozomide comprising: a) providing i) tumor cells, ii) a first formulation comprising a compound suspected of potentiating temolozomide and iii) a second formulation comprising temozolomide; b) contacting said cells with said first formulation; c) contacting said cells with said second formulation; and d) measuring the growth and death rates of said cells.

The present invention contemplates a method of screening for compounds that augment the anti-tumor effect of temolozomide comprising: a) providing i) an experimental animal and ii) tumor cells; iii) a first formulation comprising a compound suspected of potentiating temolozomide and iv) a second formulation comprising temozolomide; b) contacting said tumor cells with said experimental animal in such a way so that the tumor cells will grow in said animal so to make an animal with cancer; c) administering said first formulation to said animal with cancer; d) administering said second formulation to said animal with cancer; and e) measuring the growth and death rates of said cancer cells.

It is not intended that the present invention be limited by the nature of the compounds to be screened in the screening assay of the present invention. For example, a variety of compounds including peptides, organic compounds and nonorganic compounds, are contemplated. Additionally, combinations of compounds are contemplated by the present invention.

DESCRIPTION OF THE FIGURES

FIG. 3. Inhibitors of PARP enhance cytotoxicity of TMZ in MMR wt SW480 cells. A. Cells were treated with 0–1500 TMZ for 2 h or TMZ and 100 μM PD128763 or plus 10 μM BG for 2 h prior to 2 h exposure to TMZ. (■), TMZ alone; (♦), BG plus TMZ; (●), PD128763 plus TMZ; (▲), BG and TMZ plus PD128763. B. Cells were treated with 0–1500 μM TMZ for 2 h or TMZ and 10 μM 6-AN (pretreated for 48 h) or plus 10 μM BG for 2 h prior to 2 h exposure to TMZ. (■), TMZ alone; (♦), BG plus TMZ; (●), 6-AN plus TMZ; (▲), BG and TMZ plus 6-AN. C. Cells were treated with 0–1500 μM TMZ for 2 h or TMZ and 3 mM 3-AB (pretreated for 24 h) or plus 10 μM BG for 2 h prior to 2 h exposure to TMZ. (■), TMZ alone; (♦), BG plus TMZ; (●), 3-AB plus TMZ; (▲), BG and TMZ plus 3-AB. Results are the mean ±SD of at least three separate experiments performed in duplicate.

FIG. 4. Inhibitors of PARP enhance cytotoxicity of TMZ in MMR deficient HCT116 cells. A. Cells were treated with 0–1500 TMZ for 2 h or TMZ and 100 μM PD128763 or plus 10 μM BG for 2 h prior to 2 h exposure to TMZ. (■), TMZ alone; (♦), BG plus TMZ; (●), PD128763 plus TMZ; (▲), BG and TMZ plus PD128763. B. Cells were treated with 0–1500 μM TMZ for 2 h or TMZ and 100 μM 6-AN (pretreated for 48 h) or plus 10 μM BG for 2 h prior to 2 h exposure to TMZ. (■), TMZ alone; (♦), BG plus TMZ; (●), 6-AN plus TMZ; (▲), BG and TMZ plus 6-AN. C. Cells were treated with 0–1500 μM TMZ for 2 h or TMZ and 3 mM 3-AB (pretreated for 24 h) or plus 10 μM BG for 2 h prior to 2 h exposure to TMZ. (■), TMZ alone; (♦), BG plus TMZ; (●), 3-AB plus TMZ; (▲), BG and TMZ plus 3-AB. Results are the mean ±SD of at least three separate experiments performed in duplicate.

FIG. 5. Synergy analysis of the interaction between TMZ and MX (A) or PD128763 (B) in HTC116 cells.

FIG. 8. Distribution of cell cycle and apoptosis in colon cancer cell lines after treatment with TMZ plus modifiers. Panels A–J project data from MMR wt SW480 cells. Panels K–T project data from My deficient HCT116 cells.

DEFINITIONS

Figure 1B:
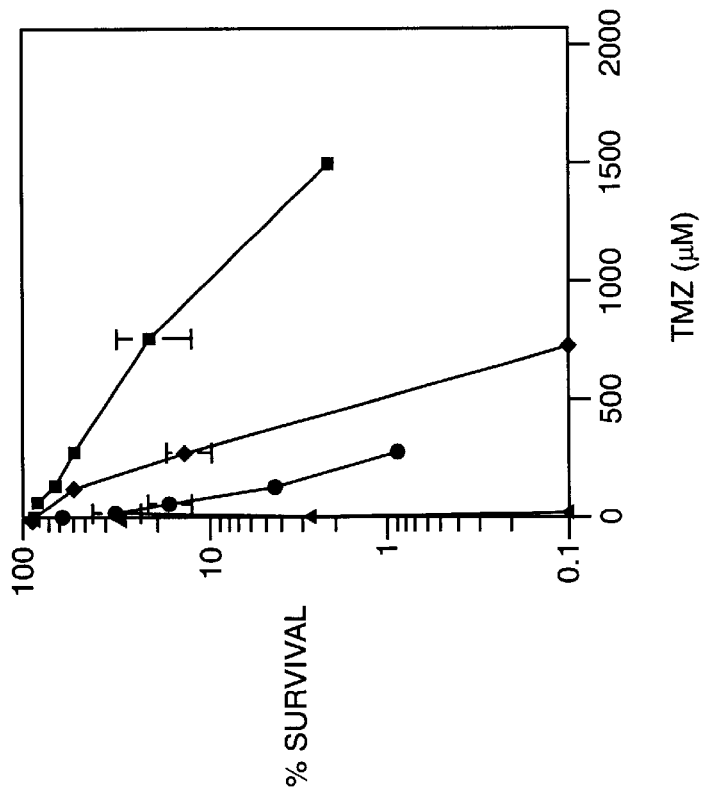
FIG. 1. MX increases the sensitivity of colon cancer cells to TMZ. Cells were treated with 0–1500 μM TMZ for 2 h or TMZ and 6 mM MX or plus 10 μM BG for 2 h prior to 2 h exposure to TMZ. A. HTC116 cells; B. SW480 cells. (■), TMZ alone; (♦), MX plus TMZ; (●), BG plus TMZ; (▲), BG and MX plus TMZ. Results are the mean ±SD of at least three separate experiments performed in duplicate.

To facilitate understanding of the invention, a number of terms are defined below.

As used herein "agent" or "drug" is used herein to denote a chemical compound, a mixture of chemical compounds, a biological macromolecule, or an extract made from biological materials such as bacteria, plants, fungi, or animal (particularly mammalian) cells or tissues that are suspected of having therapeutic properties. The agent or drug may be purified, substantially purified or partially purified.

As used herein "agonist" refers to molecules or compounds which mimic the action of a "native" or "natural" compound. Agonists may be homologous to these natural compounds in respect to conformation, charge or other characteristics. Thus, agonists may be recognized by, e.g., receptors expressed on cell surfaces. This recognition may result in physiologic and/or biochemical changes within the cell, such that the cell reacts to the presence of the agonist in the same manner as if the natural compound was present.

As used herein "antagonist" refers to molecules or compounds which inhibit the action of a "native" or "natural" compound. Antagonists may or may not be homologous to these natural compounds in respect to conformations charge or other characteristics. Thus, antagonists may be recognized by the same or different receptors or molecules that are recognized by an agonist. Antagonists may have allosteric effects which prevent the action of an agonist (e.g., by modifying a DNA adduct, or antagonists may prevent the function of the agonist (e.g., by blocking a DNA repair molecule).

As used herein, the term "fusion protein" refers to a chimeric protein containing the protein of interest joined to an exogenous protein fragment. The fusion partner may provide a detectable moiety, may provide an affinity tag to allow purification of the recombinant fusion protein from the host cell, or both. If desired, the fusion protein may-be removed from the protein of interest by a variety. of enzymatic or chemical means known to the art.

As used herein, the term "purified" or "to purify" refers to the removal of one or more contaminants from a sample. The present invention contemplates purified compositions (discussed above).

As used herein, the term "partially purified" refers to the removal of a moderate portion of the contaminants of a sample to the extent that the substance of interest is recognizable by techniques known to those skilled in the art as accounting for a measurable amount of the mixture. Preferably, the compound of interest is at least 5% of the total preparation and up to 50% of the total preparation.

As used herein, the term "substantially purified" refers to the removal of a significant portion of the contaminants of a sample to the extent that the substance of interest is recognizable by techniques known to those skilled in the art as the most abundant substance in the mixture.

As used herein the term "portion" when in reference to a protein (as in "a portion of a given protein") refers to fragments of that protein. The fragments may range in size from four amino acid residues to the entire amino acid sequence minus one amino acid. In one embodiment, the present invention contemplates "functional portions" of a protein. Such portions are. "functional" if they contain a binding region (i.e. a region having affinity for another molecule) and such binding can take place (i.e. the binding region functions, albeit with perhaps lower affinity than that observed for the full-length protein). Such "functional portions" of the gene product are typically greater than 10 amino acids in length, and more typically greater than 50 amino acids in length, and even more typically greater than 100 amino acids in length. "Functional portions" may also be "conserved portions" of the protein. The alignment of the various gene products permit one skilled in the art to select conserved portions of the protein (i.e. those portions in common between two or more species) as well as unconserved portions (i.e. those portions unique to two or more species). In one embodiment, the present invention contemplates conserved portions 10 amino acids in length or greater, and more typically greater than 50 amino acids in length.

"Staining" shall be defined as any number of processes known to those in the field that are used to better visualize, distinguish or identify a specific component(s) and/or feature(s) of a cell or cells.

"Immunofluorescence" is a staining technique used to identify, mark, label, visualize or make readily apparent by procedures known to those practiced in the art, where a ligand (usually an antibody) is bound to a receptor (usually an antigen) and such ligand, if an antibody, is conjugated to a fluorescent molecule, or the ligand is then bound by an antibody specific for the ligand, and said antibody is conjugated to a fluorescent molecule, where said fluorescent molecule can be visualized with the appropriate instrument (e.g. a fluorescent microscope).

"Antibody" shall be defined as a glycoprotein produced by B cells that binds with high specificity to the agent (usually, but not always, a peptide), or a structurally similar agent, that generated its production. Antibodies may be produced by any of the known methodologies [Current Protocols in Immunology (1998) John Wiley and Sons, Inc., N.Y.] and may be either polyclonal or monoclonal.

"In operable combination", "in operable order" and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

"Antigen" shall be defined as a protein, glycoprotein, lipoprotein, lipid or other substance that is reactive with an antibody specific for a portion of the molecule.

"Morphology" shall be defined as the visual appearance of a cell or organism when viewed with the eye, a light microscope, a confocal microscope or an electron-microscope, as appropriate.

"Patient" shall be defined as a human or other animal, such as farm animals or laboratory animals (e.g. guinea pig or mice) capable of having cell cycle (influenced) determined diseases, either naturally occurring or induced, including but not limited to cancer.

A "wild type" (wt) cell or cell line shall be defined as a cell or cell line that retains the characteristics normally associated with that type of cell or cell line for the physiological process or morphological characteristic that is being examined. It is permissible for the cell or cell line to have non-wild type characteristics for physiological process or morphological characteristics that are not being examined as long as they do not appreciably affect the process or characteristic being examined.

GENERAL DESCRIPTION OF THE INVENTION

This invention generally relates to novel compositions and methods for the treatment of certain cancers. Additionally, this invention relates to novel compositions and methods to screen drugs useful for the treatment of certain cancers. In DNA repair competent cells, DNA adducts formed by methylating agents may be efficiently repaired or may be sites of both mutagenic and cytotoxic damage. In this process, the cellular response is specific for each of the DNA adducts formed. Perhaps the best studied is the response to $O^6$-methylguanine ($O^6$mG). This adduct may be repaired in a single step reaction by $O^6$-alkylguanine-DNA alkyltransferase (AGT), however, saturation of this protein by an excess of adducts or inhibition by $O^6$-benzylguanine (BG) results in residual adducts which are both cytotoxic and mutagenic (Pegg et al. "Structure, function and inhibition of O6-alkylguanine-DNA AGT" *Prog. Nucleic Acid Res. Mol. Biol.* 51:167–233, 1995.). Cytotoxicity results from recognition of this adduct by components of the mismatch repair (MMR) system, a 5 or 6 protein complex which recognizes $O^6$mG: thymine base pairs formed by DNA replication past $O^6$mG, and excises thymine and surrounding bases, resulting in DNA strand breaks. However, a thymine is preferentially reincorporated opposite the persisting $O^6$mG, triggering MMR function again. It has been hypothesized that this repetitive aberrant repair process increases DNA double strand breaks and acts as a trigger of apoptosis (Fink et al. "The role of DNA mismatch repair in drug resistance" *Clin. Cancer Res.* 4:1–6, 1998.).

MMR deficiency results in inability to process the $O^6$mG:T mispair. Consequently cells replicate DNA past $O^6$mG lesions without cell cycle arrest, chromosomal aberrations or apoptosis and, therefore, survive in the face of persistent DNA damage (Branch et al. "Defective mismatch binding and a mutator phenotype in cells tolerant to DNA damage" *Nature* 362:652–654, 1993; Kat et al. "An alkylation-tolerant, mutator human cell line is deficient in strand-specific mismatch repair" *Proc. Natl. Acad. Sci. USA* 90:6424–6428, 1993; Karran and Bignami "DNA damage tolerance, mismatch repair and genome instability" *Bioessays* 16:833–839, 1994; Griffin et al. "DNA mismatch binding and incision at modified guanine bases by extracts of mammalian cells: implications for tolerance to DNA methylation damage" *Biochemistry* 33:4787–4793, 1994; Liu et al. "Mismatch repair mutations override alkyltransferase in conferring resistance to temozolomide by not to 1,3-bis(2-chloroethyl)nitrosourea" *Cancer Res.* 56:5375–5379, 1996). The presence of MMR deficiency in a number of colon cancer cell lines allowed the present inventors the opportunity to evaluate the relative contribution of this DNA repair defect in resistance to the methylating chemotherapeutic agent, temozolomide (TMZ), where we found that MMR deficiency resulted in 35–60 fold resistance to TMZ in cells defective in either MLH1 or GTBP even after inhibition of AGT by BG (Liu et al. "Mismatch repair mutations override alkyltransferase in conferring resistance to temozolomide by not to 1,3-bis(2-chloroethyl)nitrosourea" *Cancer Res.* 56:5375–5379, 1996).

While $O^6$mG is the best studied cytotoxic DNA adduct, it is not the most abundant. TMZ like other methylating agents, also forms $N^7$-methylguanine ($N^7$mG) and $N^3$-methyladenine ($N^3$mA) DNA adducts at frequencies 11 and 1.5 times that of $O^6$mG (our unpublished results). These DNA adducts are efficiently removed by base excision repair (BER) and appear to contribute little to cytotoxicity. In the first step of BER, a series of glycosylases recognize abnormal bases such as $N^3$mA and $N^7$mG (O'Connor et al. "Isolation and structure of a cDNA expressing a mammalian 3-methyladenine-DNA glycosylase" *EMBO J.* 9:3337–3342, 1990; Samson et al. "Cloning and characterization of a 3-methyladenine DNA glycosylase cDNA from human cells whose gene maps to chromosome 16" *Proc. Natl. Acad. Sci. USA* 88:9127–9131, 1991), the T:G mismatch (Neddermann et al. "Cloning and Expression of Human G/T Mismatch-specific Thymine-DNA Glycosylase" *J. Biol. Chem.* 271:12767–12774, 1996), and deaminated bases such as hypoxanthine/oxidized 8-oxo-7,8-dihydroguanine or uracil:A (Vollberg et al. "Isolation and characterization of the human uracil DNA glycosylase gene" *Proc. Natl. Acad. Sci. USA* 86: 8693–8697, 1989; Olsen et al. "Molecular cloning of human uracil-DNA glycosylase, a highly conserved DNA repair enzyme" *EMBO J.* 8:3121–3125, 1989; Radicella et al. "Cloning and characterization of hOGG1, a human homolog of the OGG1 gene of *Saccharomyces cerevisiae*" *Proc. Natl. Acad. Sci. USA* 94:8010–8015, 1997; Rosenquist et al. "Cloning and characterization of a mammalian 8-oxoguanine DNA glycosylase" *Proc. Natl. Acad. Sci. USA* 94:7429–7434, 1997). Following enzymatic or spontaneous hydrolysis of the N-glycosidic bond and release of the abnormal base, AP (apurinic/apyrimidinic) endonuclease hydrolyzes the phosphodiester backbone 5' to the lesion and dRpase (a DNA deoxyribophosphodiesterase and its activity is associated with polymerase β) excises the residual dRp, generating a gap of one nucleotide. DNA polymerase β fills the gap and DNA ligase seals the nick. This pathway is called short-patch BER. An alternative pathway for BER involves DNA synthesis to fill a gap of 2 to 13 nucleotides. This long patch repair requires proliferating cell nuclear antigen (PCNA) and PCNA-dependent DNA polymerase (Willson "Mammalian base excision repair and DNA polymerase beta" *Mutation Res.* 407:203–215, 1998).

Poly-(ADP-ribose)-polymerase (PARP) acts as a nick sensor of DNA strand breaks by itself or interaction with XRCC1 and involves in BER. PARP binds damaged DNA, resulting in autoribosylation. The modified protein then releases and allows other proteins to access and repair DNA strand breaks (Willson "Mammalian base excision repair and DNA polymerase beta" *Mutation Res.* 407:203–215, 1998; Molinete et al. "Over production of the poly (ADP-ribose) polymerase DNA-binding domain blocks alkylation-induced DNA repair synthesis in mammalian cells" *EMBO J.* 12:2109–2117, 1993; Caldecott et. al "XRCC1 polypeptide interacts with DNA polymerase β and possibly poly (ADP-ribose) polymerase, and DNA ligase III is a novel molecular 'nick-sensor' in vitro" *Nucleic Acids Res.* 24:4387–4394, 1996). Therefore, PARP participates in BER after nick formation in both short patch and long patch repair. It appears most active in the alternative (long patch repair) pathway for BER.

BER as a therapeutic target to increase the cytotoxicity of methylating agents has been documented. Cells deficient in DNA polymerase β or blocked in expression of AP endonuclease by antisense oligonucleotides are sensitized-to methylating agents (Sobol et al. "Requirement of mammalian DNA polymerase-β in base-excision repair" *Nature* 379:183–186, 1996; Walker et al. "A role for the human DNA repair enzyme HAP1 in cellular protection against DNA damaging agents and hypoxic stress" *Nucleic Acids Res* 22:4884–4889, 1994). In addition, mice deficient in $N^3$-methyladenine DNA glycosylase exhibited increased sensitivity to alkylating drugs like BCNU and mitomycin C (Engelward et al. "Repair-deficient 3-methyladenine DNA glycosylase homozygous mutant mouse cells have increased sensitivity to alkylation-induced chromosome damage and cell killing" *EMBO* 15:945–952, 1996). Oni the other hand, overexpression of the $N^3$-methyladenine DNA glycosylase, which increases the number of AP sites formed, -also increases the cytotoxicity of methylating agents (Coquerelle et al. "Overexpression of N-methylpurine-DNA glycosylase in Chinese hamster ovary cells renders them more sensitive to the production of chromosomal aberrations by methylating agents—a case of imbalanced DNA repair" *Mutation Res.* 336:9–17, 1995.) Finally, cells lacking PARP activity are more sensitive to alkylating agents, with increased apoptosis and chromosomal instability (Menissier-de Murcia et al. "Requirement of poly (ADP-ribose) polymerase in recovery from DNA damage in mice and in cells" *Proc. Natl. Acad. Sci. USA* 94:7303–7304, 1997; Boulton et al. "Potentiation of temozolomide-induced cytotoxicity: a comparative study of the biological effects of poly (ADP-ribose) polymerase inhibitors" *Br. J Cancer,* 72:849–856, 1995). These data suggest that balanced expression of proteins in the base excision repair complex is important to the efficient processing of lesions. BER is an important mechanism of:resistance to therapeutic methylating agents.

We examined two classes of agents which could inhibit the BER pathway to determine whether they would increase the cytotoxicity of methylating agents in colon cancer cells, particularly in cells deficient in MMR. Since ME deficient cells are tolerant to $O^6$mG formed by TMZ, any change in cytotoxicity observed after use of a BER inhibitor would be due to interruption in repair of $N^7$mG and $N^3$mA DNA adducts. Our first strategy was to combine methoxyamine (MX) with TMZ. MX has been shown to react with the free aldehyde formed at the abasic site exposed by glycosylases and to reduce cleavage at AP sites in mammalian cells, suggesting that the MX bound abasic site is not-a substrate for AP endonuclease (Fortini et al. "Mutagenic processing of ethylation damage in mammalian cells: the use of methoxyamine to study apurinic/apyrimidinic site-induced mutagenesis" *Cancer Res.* 53:1149–1155, 1993). In the regard that AP sites modified by MX are relatively stable and must be converted to cytotoxic lesions, we hypothesized that MX would interrupt BER in cells and potentiate the cytotoxic effects of TMZ, even in MMR defective cells. The second strategy we used was to inhibit PARP with 3,4-dihydro-5-methyoxyisoquinoline-1 (2H)-one (PD128763), 3-aminobenzamide (3-AB) or 6-aminonicotinamide (6-AN) and to subsequently treat cells with TMZ. We hypothesize that inactivated PARP would affect short and long patch BER, destabilize strand breaks, reduce interaction with other proteins during repair of methylated DNA adducts and lead to cell death, again,- in both MMR proficient and deficient cells.

As contemplated above, since MMR defective cell lines are remarkably resistant to methylating agents yet accumulate high levels of 3 methylating DNA adducts, $O^6$mG, $N^3$mA and $N^7$mG, we reasoned that the interruption of repair of N3mA and $N^7$mG adducts by the BER process would sensitize cells to methylating agents. To address this issue, we studied the effect of MX on potentiation of TMZ-cytotoxicity. MX interacts specifically with the tautomeric open-ring form of deoxyribose generated from the removal of an abnormal base by glycosylase. The MX modified AP site is relatively stable (Liuzzi and Talpeart-Borle "A new approach to the study of the base-excision repair pathway using methoxyamine" *J. Biol. Chem.* 260:5252–5258, 1985; Rosa et al. "Processing in vitro of an abasic site reacted with methoxyamine: a new assay for the detection of abasic sites formed in vivo" *Nucleic Acids Res.* 19: 5569–5574, 1991) and inhibits the cleavage of AP sites in DNA by AP endonuclease in mammalian cells. This has been shown to protect cells from cytotoxicity, mutagenicity induced by S$_N$1-type ethylating agents, such as ENU but not, S$_N$2 alkylating agent, diethylsulfate and MMS (Fortini et al. "Mutagenic processing of ethylation damage in mammalian cells: the use of methoxyamine to study apurinic/apyrimidinic site-induced mutagenesis" *Cancer Res.* 53: 1149–1155, 1993; Fortini et al. "Methoxyamine modification of abasic sites protects CHO cells from the cytotoxic and mutagenic effects of oxygen alkylation" *Carcinogenesis* 13: 87–93, 1992). Moreover, the protection was strictly time-dependent and was limited to the short period (30 min) after exposure to the alkylating agents (Fortini et al. "Methoxyamine modification of abasic sites protects CHO cells from the cytotoxic and mutagenic effects of oxygen alkylation" *Carcinogenesis* 13: 87–93, 1992).

In our initial studies, we observed that MX reduced cleavage at AP sites and decreased BER in human colon cancer cell extracts. However, we did not see protection of these two cell lines from ENU cytotoxicity using longer duration exposure to MX. The short duration of MX studied previously may not have the same impact on BER inhibition as does a longer exposure to MX. Our results showed that MX synergistically increased TMZ-induced cytotoxicity in human colon cancer cell lines in both M proficient and deficient cells. A similar degree of enhanced cytotoxicity was observed with MX and MMS and with TMZ as well. The effect of BG inhibition of AGT was additive to the effect of MX only in the M proficient SW480 cell line but not in the MMR defective HCT116 cell line. These data suggest that $O^6$mG DNA adducts do not contribute to the enhanced cytotoxic effect of TMZ by MX. Furthermore, a similar degree of enhanced cytotoxicity was observed with MX and MMS as with TMZ, again implicating $N^3$mA and $N^7$mG induced abasic sites as the major targets for MX. In our recent studies, a prolonged exposure to low dose MX results in even greater potentiation of TMZ cytotoxicity.

The mechanisms of MX-enhanced cytotoxicity of methylating agents in colon cancer cells have not been fully understood. It is fair to suggest that MX enhanced the cytotoxic effect of TMZ due to i). the MX-AP site complex is able to block the AP endonucleolytic step of the BER pathway; ii). The persistence of abasic sites may increase topoisomerase II mediated DNA cleavage (Kingma and Osheroff "Apurinic sites are position-specific topoisomerase II poisons" *J. Biol. Chem.* 272: 1148–1155, 1997); iii). AP sites inhibit DNA replication and trigger programmed cell death (Robertson et al. "Down-regulation of apurinic/ apyrimidinic endonuclease expression is associated with the induction of apoptosis in differentiating myeloid leukemia cells" *Cell Growth & Differentiation* 8: 443–449, 1997).

Under normal circumstances, TMZ produces strand breaks during BER mediated repair of $N^7mG$ and $N^3mA$ adducts which are efficiently repaired and do not contribute to cytotoxicity until high concentrations of adducts are achieved. When DNA strand breaks are present, one component of the response is recognition, binding and activation of PARP. Activated PARP leads to autoribosylation, and this in turn facilitates access of repair enzymes to DNA damage (Willson "Mammalian base excision repair and DNA polymerase beta" *Mutation Res.* 407: 203–215, 1998; Buschfort et al. "DNA excision repair profiles of normal and leukemic human lymphocytes: functional analysis at the. single-cell level" *Cancer Res.* 57: 651–658, 1997) and appears to enhance processing of stand breaks and religation by polymerase-β and ligase I (Althaus et al. "Histone shuttle driven by the automodification cycle of poly(ADP-ribose) polymerase". *Environ Mol Mutagen,* 22: 278–282, 1993). In the alternative BER pathway, PARP interacts with XRCC1 to facilitate repair (Caldecott et al. "XRCC1 polypeptide interacts with DNA polymerase β and possibly poly (ADP-ribose) polymerase, and DNA ligase III is a novel molecular 'nick-sensor' in vitro" *Nucleic Acids Res.* 24: 4387–4394, 1996). It seems likely that PARP plays an important role in communication between repair proteins and stability of the repair complex involved in BER. This suggests that inhibition of PARP leads to an impaired ability to rejoin DNA strand breaks which can initiate both apoptotic and non-apoptotic cell death cascades and thereby increase cytotoxicity of TMZ (Wedge et al. "3-Aminobenzamide and /or $O^6$benzylguanine evaluated as an adjuvant to temozolomide or BCNU treatment in cell lines of variable mismatch repair status and $O^6$-alkylguanine-DNA alkyltransferase activity" *Br. J Cancer* 74: 1030–1036, 1996). Our results support this hypothesis. Potentiation of cytotoxicity of methylating agent with PARP inhibitors was observed with a marked increase in apoptosis and PARP cleavage.

Results of BCNU combined with either MX or PD128763 are in sharp contrast to TMZ; little if any potentiation is observed in the absence of BG in either cell line. This suggests that while BER appears to process BCNU induced crosslinks, inhibition of BER in this manner has little impact on BCNU toxicity. One of the best studied BCNU-induced lethal lesions is the $N^3C$—$N^1G$ interstrand cross-link formed after initial chloroethyl monoadducts at $O^6G$ and cyclic rearrangement to $N^1$, $O^6$-ethanoguanine (Wilson et al. "Life without DNA repair" *Proc. Natl. Acad. Sci. USA* 94: 12754–12757, 1997). However, treatment of cells with BCNU also produces alkylated bases that may be labile and spontaneously result in breakage or nicking of the phosphoribosyl backbone (Gonzaga et al. "Identification of the cross-link between human $O^6$-methylguanine-DNA methyltransferase and chloroethylnitrosourea-treated DNA" *Cancer Res.* 52:6052–6058, 1992). Since PARP has been shown to bind to BCNU-induced DNA nicks in vitro (Prakash and Gibson "Sequence-selective depurination, DNA interstrand cross-linking and DNA strand break formation associated with alkylated DNA" *Carcinogenesis* 13: 425–431, 1992), it is reasonable to assume that PD128763 might increase BCNU-cytotoxicity. However, our studies showed only minor enhancement of toxicity in HCT116 cells and no enhancement in SW480 cells. Even though methyladenine DNA glycosylase has been implicated in BCNU cross-link repair and its absence sensitizes cells to BCNU (Malapetsa et al. "Identification of a 116 kDa protein able to bind 1,3-bis(2-chloroethyl)-1-nitrosourea-damaged DNA as poly (ADP-ribose) polymerase" *Mutation Res.* 362: 41–50, 1996), we did not observe sensitization to BCNU by treatment with MX in the absence of BG. In the presence of BG, MX potentiated BCNU toxicity, indicating that MX may interfere with DNA cross-link repair pathway and suggesting that BER may be involved in repair of the $N^1O^6$ethanoguanine cross-link which is not formed if AGT reacts with the $O^6$chloroethylguanine adduct. Taken together, these data suggest a different reaction of MX with damaged DNA induced by BCNU compared to TMZ. With TMZ, MX-increased cytotoxicity is associated with AP sites generated from repair of $N^7mG$ and $N^3mA$ DNA adducts formed by methylating agent but with BCNU, it might be the $O^6$ lesion induced cross-link which controls BCNU toxicity.

While an understanding of the precise mechanism is not needed to practice the present invention, it appears that the apoptosis mediates both Mx and PD128763-enhanced cytotoxicity of TMZ. Increased apoptosis was observed in MMR wt SW480 cells but not in M deficient HCT116 cells after treatment with BG and TMZ. This suggests that MMR processing of $O^6mG$ is a potent apoptosis-inducing event (Matijasevic et al. "Protection against chloroethylnitrosourea cytotoxicity by eukaryotic 3-methyladenine DNA glycosylase" *Proc. Natl. Acad. Sci. USA,* 90:11855–11859, 1993). Although the biological and functional consequences of PARP and its cleavage in apoptosis. still remain to be further identified, it has been demonstrated that PARP is rapidly and specifically cleaved during apoptosis (Kaina et al. "Chromosomal instability, reproductive cell death and apoptosis induced by $O^6$-methylguanine in Mex−, Mex+ and methylation-tolerant mismatch repair compromised cells: facts and models" *Mutation Res.* 381: 227–241, 1997; Lindahl et al. "Post-translational modification of poly(ADP-ribose) polymerase induced by DNA strand breaks" *Trends Biochem Sci* 20: 405–411, 1995). PARP cleavage was observed in both SW480 and HCTI 16 cells after treatment with either MX or one of the PARP inhibitors and TMZ, confirming activation of apoptotic pathways.

We noted that arrest at cell cycle checkpoints paralleled the cellular response to DNA damage and that these were dependent on MMR and BER pathways. MMR wt SW480 cells were sensitive to TMZ alone with arrest in the S and G2 phases (Fink et al. "The role of DNA mismatch repair in drug resistance" *Clin. Cancer Res.* 4: 1–6, 1998). The S and G2 arrest were potentiated by MX or by PD128763 despite the fact that SW480 is a p53 mutant cell line. In contrast, even high levels of DNA adducts formed by TMZ in the MMR deficient HCT116 cells did not induce cell cycle checkpoint arrest despite the fact that p53 is wild type in this cell line. This dysregulation of damage-induced cell cycle checkpoint control appeared due to failure of processing $O^6mG$ lesions in MMR deficient cells. However after combined treatment with TMZ and either MX or PD 128763, HCT116 cells showed S/G2 phase arrest and apoptosis. These results are consistent with previous studies of cell cycle changes following MMS exposure or other compounds that produce 90% $N^3mA$ (Lazebnik et al. "Cleavage of poly(ADP-ribose) polymerase by a proteinase with properties like ICE". *Nature* 371: 346–347, 1994; Morris et al. "Flow cytometric evaluation of cell-cycle progression in ethyl methanesulfonate and methyl methanesulfonate-exposed P3 cells: relationship to the induction of sister-chromatid exchanges and cellular toxicity" *Environ. Mol. Mutagen.* 18: 139–149, 1991) and the prolonged G2 arrest observed in PARP knockout mice or derived cell lines (Menissier-de Murcia et al. "Requirement of poly (ADP-ribose) polymerase in recovery from DNA damage in mice and in cells" *Proc. Natl. Acad. Sci. USA* 94: 7303–7304, 1997) following DNA damage. These data indicate that both SW480 and HCT116 cells have a similar response to persistent $N^7mG$ and $N^3mA$ lesions, following interruption of BER.

Again, while an understanding of the mechanism is not necessary to practice the invention, it appears that disrupted BER processing of non $O^6mG$, most likely $N^7mG$ and $N^3mA$ DNA adducts formed by TMZ is cytotoxic to colon cancer cell lines. This may be particularly important in MMR deficient cells which are resistant to TMZ alone due to the failure to recognize $O^6mG$ DNA adducts. These studies provide evidence that disrupting repair of $N^7mG$ and $N^3mA$ by inhibiting BER or PARP may improve the therapeutic efficacy of methylating agents.

DETAILED DESCRIPTION OF PREFERRED EMBODIMENTS

Generally, the nomenclature used hereafter and the laboratory procedures in cell culture, tissue culture, tumor biology, and molecular genetics described below are those well known and commonly employed in the art. Standard techniques are used for cell culture methods, experimental design and compound formulation and nomenclature. Generally chemical reactions and purification steps are performed according to the manufacturer's specifications. The techniques and procedures are generally performed according to conventional methods in the art and various general references (see, generally, Sambrook et al. Molecular Cloning: A Laboratory Manual, 2d ed. (1989) Cold Spring Harbor Laboratory Press, Cold Spring Harbor, N.Y., and Current Protocols in Molecular Biology (1996) John Wiley and Sons, Inc., N.Y., which are incorporated herein by reference) which are provided throughout this document. All the information contained therein is incorporated herein by reference.

Assays for detecting the ability of agents to inhibit or enhance TMZ-mediated tumor reduction provide for facile high-throughput screening of agent banks (e.g., compound libraries, peptide libraries, and the like) to identify potentiator. Such TMZ potentiator may be further developed as potential therapeutics and diagnostic or prognostic tools for diverse types of cancers. Likewise, TMZ and various potentiator may be useful in the treatment or diagnostics of other diseases. For example, such combinations of drugs may be directed to virally or parasitically infected cells Thus, the present invention provides a method for potentiating the toxicity of temolozomide in human cancer cells by administering an APE or a PARP inhibiting amount of an APE or PARP inhibitor. The present invention also provides a product comprising temolozomide and an APE or PARP inhibitor as a combined preparation. for simultaneous, separate or sequential administration in said treatment of human caner cells. Additionally the present invention provides a method for the screening of compounds that may potentiate the toxicity of temolozomide by the mechanisms of inhibiting APE or PARP, or by other mechanisms.

I. Potentiation of Temozolomide Treatment for Cancer

The present invention contemplates compositions and methods for the potentiation of the elimination of cancer cells by temozolomide. Wjile not limiting the invention to any particular mechanism, it is believed that temozolomide works as an anticancer agent by producing the DNA adducts $O^6mG$, $N^7mG$ and $N^3mA$. An accumulation of adduct results in the apoptotic elimination of the cell. However, the $O^6mG$ adducts are typically repaired by the MMR system and the $N^7mG$ and $N^3mA$ adducts are typically repaired by the base excision repair (BER) system. After removal of the abnormal base by methylpurine glycosylase, AP endonuclease (APE) cleaves the back bone and removes the sugar, allowing DNA repair. If the number of adducts produced outstrips the cells ability to repair the damage, or the BER repair mechanism is rendered ineffective, damage will accumulate and the cell will be eliminated through an apoptotic mechanism. Methoxyamine reacts with the abasic site and prevents APE cleavage, disrupting DNA repair. Methoxyamine has been shown in the present invention to potentiate the activity of temolozomide in the treatment of cancer. PARP aids in the repair of DNA strand breaks induced during MMR and BER. As such, inhibitors of PARP activity have been shown in the present invention to be effective in potentiating the activity of temolozomide in the elimination of cancer cells. The effectiveness of temozolomide as an anticancer agent can be greatly enhanced when used in conjunction with a potentiator that prevents the repair of the DNA adducts created as a result of treatment of the cell with temolozomide.

Temozolomide has been found to be most preferably administered in repeat dosages on consecutive days, and the dramatic potentiation effects of the present invention are realized in the highly preferred regimen involving the administration of MX or a PARP inhibitor prior to, or concurrent with, the administration of each dose.

Preferably, this administration of an APE or PARP inhibitor is repeated over a period of several days and is prior to the administered doses of temolozomide. Repeat doses can be administered at 1, 2, 3, 4 or 5 days or more with the preferred period of therapy determined by the response of the tumor to the treatment.

In a preferred embodiment, the APE or PARP inhibitor is administered in an APE or PARP inhibiting amount, i.e. an amount sufficient to sensitize the tumor in vivo without causing undue sensitization of normal tissue, when the APE or PARP inhibitor is used concurrently with temozolomide.

The amount of the APE or PARP inhibitor used in the present invention varies according to the degree of the effective amount required for the treating of tumor cells. A suitable dosage is that which will result in a concentration of the APE or PARP inhibitor in the tumor cells to be treated which results in the depletion of the APE or PARP activity, respectively. If desired, some tumor cells can be obtained by biopsy and can be tested in vitro for their sensitivity prior to in vivo treatment.

The neoplasms for which temolozomide is a particularly suitable treatment include carcinomas, melanomas, sarcomas, lymphomas and leukaemias, with specific utility for astrocytoma, gliomas, malignant melanoma, chronic lymphocytic leukaemia, lung cancer and breast cancer.

Typical dosage ranges of temolozomide are generally between 0.1 and 200, preferably between 1 and 20 mg/kg body weight per day. The amount of APE inhibitor or PARP inhibitor necessary for the potentiation of temolozomide is dependent upon the amount of APE or PARP, respectively, normally present in the cancer cell type. A cancer cell having higher levels of APE or PARP will be potentiated more dramatically by the preadministration or simultaneous administration of the APE or PARP inhibitor. Additionally, the amount of APE or PARP inhibitor necessary depends on the age and condition of the patient, the severity of the cancer being treated and the particular inhibitor being utilized.

II. Drug Screens

As noted above, the present invention contemplates screening assays for identifying compounds that inhibit tumor growth. The present invention contemplates a screening assay utilizing cell lines that are resistant to temolozomide to screen for compounds that potentiate the anticancer properties of temolozomide. In one embodiment, a temolozomide resistant cell line is pretreated with the compound suspected of potentiating the anticancer properties of temolozomide followed by treatment with temozolomide. Cell growth and/or apoptosis are then measured. In another embodiment, the compound suspected . of potentiating the anticancer temozolomide is given simultaneously with temozolomide.

Additionally, the present invention contemplates the screening of compounds by the use of xenographs. In one embodiment, tumor cells are injected into immune compromised mice (or other suitable animal) and allowed to grow. Mice carrying the tumors are then treated with the compound suspected of potentiating temozolomide in parallel with or prior to treatment with temozolomide. Tumor size is then measured to follow the effect of the treatment.

It is not intended that the present invention be limited by the nature of the drugs screened in the screening assay of the present invention. A variety of compounds, including peptides, organic compounds, nonorganic compounds, as well as, formulations of more than one compound, are contemplated.

It is also not intended that the present invention be limited by the particular tumor cells used for the drug testing. A variety of tumor cells (for both positive and negative controls) are contemplated (including but not limited to cells set forth above and in the examples below).

It is also not intended that the present invention be limited by the mechanism by which the compound suspected of potentiating TMZ works. For example, the compound may work by inhibiting APE cleavage, by inhibiting other DNA repair mechanisms (e.g. PARP) or by other as of yet unidentified mechanisms.

It is contemplated that the invention be utilized in the screening of compounds by high-throughput screening methods. For example, automated systems and microscale assay systems are contemplated. Furthermore, it is contemplated that the invention can be used for the screening of compound libraries (e.g. drug libraries) utilizing these high throughput screening methods.

Experimental

Materials and Methods

Chemicals and Reagents. BG was generously provided by Dr. Robert Moschel (Frederick Cancer Research and Development Center, National Cancer Institute). Stock solution was made in dimethylsulfoxide. TMZ and BCNU were obtained from the Drug Synthesis and Chemistry Branch, Drug Therapeutic Program, National Cancer Center Institute. PD128763 was a gift from Park-Davis Pharmaceutical Division. 6-AN, 3-AB, MX and methylmethane sulfonate (MMS) were purchased from Sigma (ST. Louis, Mo.). Stock solutions of PD128763, 3-AB and 6-AN were prepared by dissolving in dimethylsulphoxide and added to cell culture at a final concentration of <1% DMSO, when cells were treated with these compounds. MX was dissolved in sterilized water (PH 7.0). All stock solutions were kept in −20° C. BCNU was prepared fresh in 0.5 ml of 100% ethanol, diluted in PBS, and used with in 10 min.

Colony Survival Assay. SW480 cells were obtained from the ATCC. HCT116 cells were obtained from R. Boland, University of Michigan Medical Center. All cell lines were cultured in appropriate growth medium.

Cells (2000/dish) were plated, adhered for 18 hrs and treated with TMZ or MMS plus or minus modifiers such as BX, MX, 6-AN, 3-AB or PD128763, according to experimental protocol. After treatment, cells were washed and fresh medium was replaced. The cells were grown for a further 7 days prior to staining with methylene blue for determination of colonies containing more than 50 cells. Comparisons of drug induced cytotoxicity consisted of a calculation of the dose modification factor (DMF), defined as the ratio of the $IC_{50}$ of either TMZ or MMS in the absence to that in the presence of indicted modifier(s), i.e. DMF= $IC_{50}$ for TMZ alone $IC_{50}$ for TMZ plus modifier(s).

Median Effect Analysis (MEA). MEA was used to determine the dose-response interactions between TMZ and either MX or PD128763. Drugs were combined at the ratio of the $IC_{50}$ values for either TMZ and MX or TMZ and PD128763 as determined by survival / concentration curves. The combination was compared to the cytotoxicity of each drug alone in every experiment. The combination index (CI) was determined from colony-forming assays at increasing levels of cell killing, using analysis of multiple drug interaction program (Biosoft, Cambridge, United Kingdom) developed based on method of Chou and Talalay (Chou and. Talalay "Quantitative analysis of dose-effect relationship: the combined effects of multiple drugs on enzyme inhibitors" In: G. Weber (ed.) *Advances in Enzyme Regulation, pp.* 27–55, New York: Pergamon Press, 1983). CI values of less than or grater than 1 indicate synergy and antagonism, respectively., whereas a CI value of 1 indicates additivity of the drugs.

Flow Cytometry for Cell Cycle Distribution Analysis. For cell cycle analysis, $10^6$ cells were plated in 100-mm tissue culture dishes and exposed to MX (6 mM)/PD128763 (100 μM) or MX (6 mM)/PD128763 (100 μM) plus TMZ (300M) at 37° C. After 24h–72h of culture, cells were fixed in 80% ethanol and DNA was stained with 20 μg/ml propidium iodide. DNA fluorescence of PI-stained cells was measured with an Elite. ESP flow cytometer/cell sorter (Coulter, Miami, Fla.). Cell cycle distribution was analyzed with Modfit 5.2 program (Verity software, Topsham, Mass.) at least 10,000 cells per data point.

Western Blotting for PARP Cleavage Detection. Cell extracts were resolved by SDS-PAGE (12% polyacrylamide) in a Bio-Rad minigel apparatus at 150 V for 1 hr. Proteins were transferred onto PVDV membranes, using a Bio-Rad mini Trans-Blot cell for 1 hr at 100 V. The blotted membranes were blocked with 5% dry milk in TBS buffer and then probed for 2 hr with anti-PARP antibody C2-10 (Trevigen, Gaithersburg, Md.). After three 5 min washes with TBS-Tween20 (0.05%), the blots were incubated with secondary antibody, anti-mouse HRPO-anti IgG for 1 hr (Amersham Life Science, Arlington Height Ill.). Antibody binding was visualized by ECL according to manufacturer's instructions (Amersham Life Science, Arlington Heights, Ill.).

Tumors in Nude Mice. Tumor cells ($5 \times 10^6$) were injected into flanks of female athymic HSD nude mice, at 6–8 weeks of age. The tumors were measured with calipers using the National Cancer Institute formula: $V=L$ (mm)$\times I^2$(mm)/2 where L is the largest diameter and I is the smallest diameter of the tumor. When the volume of the nodules has achieved about 100–150 mm$^3$, tumor-bearing mice were assigned randomly for the control or treatment groups (3–5 mice/group).

Antitumor Effects of TMZ and MX plus TMZ. Nude mice carrying tumors were received TMZ, MX or MX combined with TMZ daily for a period of 5 days of treatment. Doses used per group were as follows: a). TMZ alone, 120 mg/kg; b) MX alone, 2 mg/kg; c) BG plus TMZ, 30 mg/kg BG+120 mg/kg; d) MX plus TMZ, 0.2 mg/kg MX+120 mg/kg TMZ.

Experimental End Point. Tumor measurements were taken every 3 days. The relative tumor volume ($V/V_O$) was calculated by dividing the measured tumor volume (V) by the initial tumor volume ($V_O$) at day 0. Tumor responses were quantified by tumor regrowth delay. Tumor growth delays were calculated according to: tumor growth delay= $T_{2x} - C_{2x}$, where $T_{2x}$ and $C_{2x}$ represent the number of days treated and control tumors take to double in size from the day of treatment, respectively.

Toxicity Evaluation. Toxicity after treatment was evaluated by body weight measurements and peripheral WBC counting. Body weight was measured three times weekly from the first treatment until 2 weeks after the end of treatment. The weight loss was expresses as a percentage of the initial weight (initial weight–lowest weight/initial weight$\times$100%). Peripheral WBCs were monitored 5 days after the end of treatment compared with WBCs of control mice.

EXAMPLE I
Methoxyamine Potentiates Cytotoxicity of TMZ

Figure 1A:
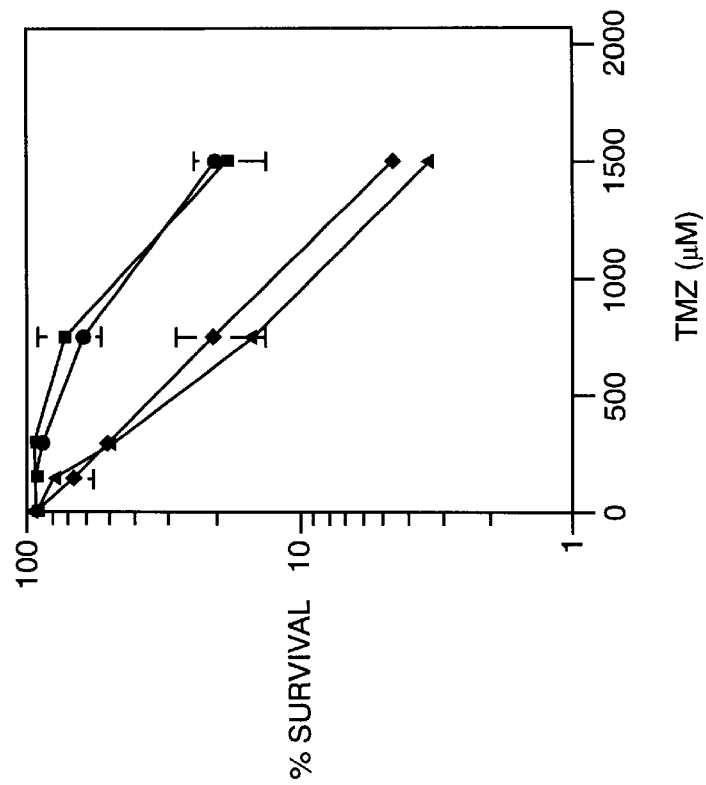

We have previously reported the comparative cytotoxicity of TMZ and BG in the SW480 and HCT116 cells lines (Liu et al. "Mismatch repair mutations override alkyltransferase in conferring resistance to temozolomide by not to 1,3-bis (2-chloroethyl)nitrosourea" *Cancer Res.* 56: 5375–5379, 1996). In order to test whether MX would alter TMZ cytotoxicity, we treated SW480 and HCT116 with 6 mM MX (itself a nontoxic concentration) plus TMZ (0–1500 $\mu$M) for 2 hr, with or without BG to abolish AGT mediated removal of O$^6$mG DNA adducts. SW480 cells were moderately resistant to TMZ, with an IC$_{50}$ of 395 $\mu$M which was reduced 14 fold to 28 $\mu$M by BG pretreatment. Greater resistance to TMZ was observed in MH1 defective cells, even after inhibition of AGT by BG (IC$_{50}$, 950 $\mu$M). In both cell lines, MX potentiated the cytotoxic effect of TMZ with a DMF of 2.4 in SW480 and 3.1 in HCT116 (FIG. 1). In SW480 cells, additive effects of MX and BG were noted (IC$_{50}$ was reduced from 395 $\mu$M to 6 $\mu$M), whereas, with HCT116 cells no effect of BG was seen in the presence of MX (FIG. 1: A. HTCl16 cells; B. SW480 cells. (■), TMZ alone; (♦), MX plus TMZ; (●), BG plus TMZ; (▲), BG and MX plus TMZ).

Figure 2B:
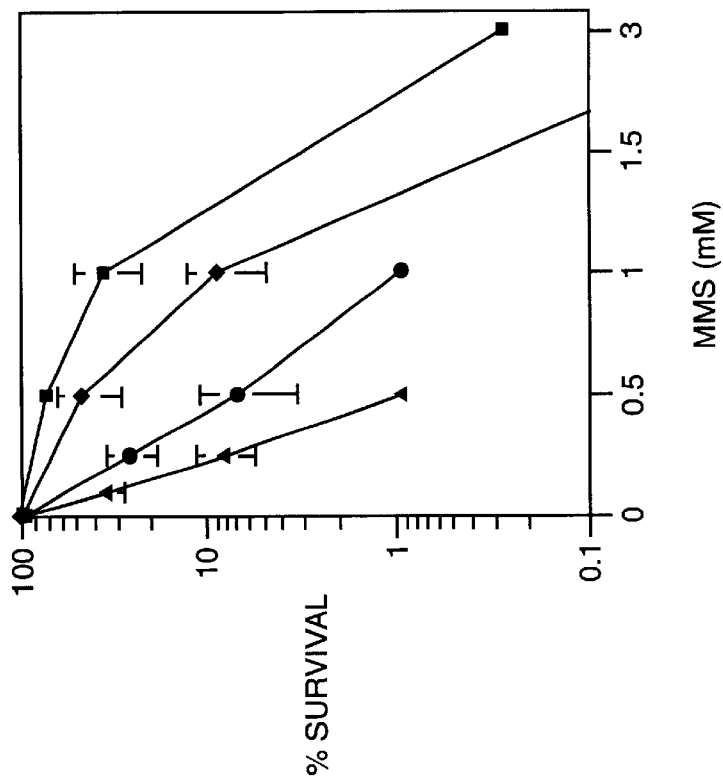
FIG. 2. Cytotoxicity of MMS enhanced by MX in colon cancer cell lines. Cells were treated with 0–3 mM MMS for 1 h or MMS and 6 mM Mx plus 10 μM BG for 2 h prior to 2 h exposure to MMS. A. HCT116 cells; B. SW480 cells. (■), MMS alone; (♦), MX plus MMS; (●), BG plus MMS; (▲), BG and MX plus MMS. Results are the mean ±SD of at least three separate experiments performed in duplicate.
Figure 2A:
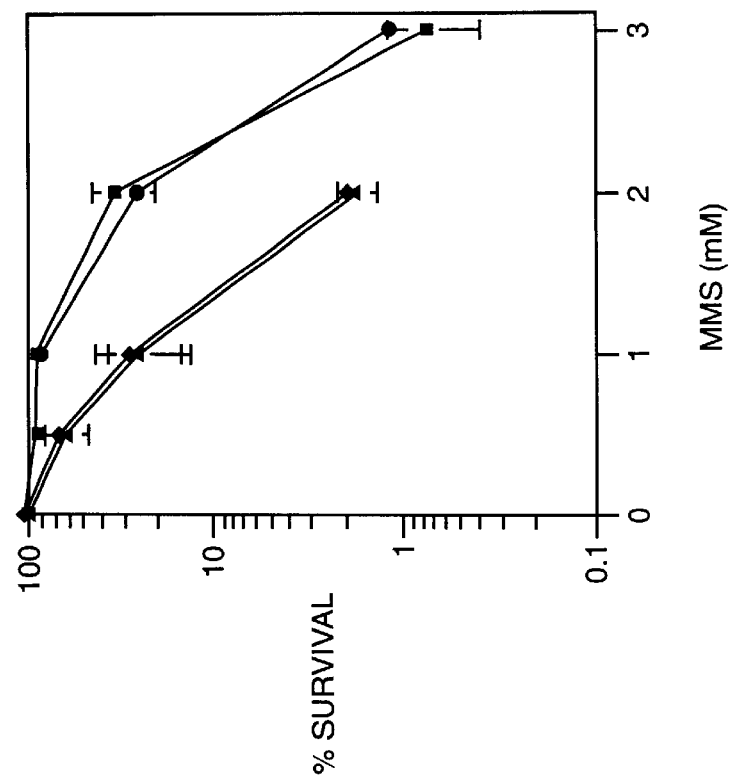

To further decipher the role of N$^3$mA and N$^7$mG DNA adducts in the relative absence of O$^6$mG, we evaluated the effect of MX on MMS mediated cytotoxicity. MMS is a methylating agent which produces far fewer O$^6$mG adducts (0.3%) and a greater proportion of N$^3$mA (10%) and N$^7$mG adducts (87%) than TMZ (Chou and Talalay "Quantitative analysis of dose-effect relationship: the combined effects of multiple drugs on enzyme inhibitors" In: G. Weber (ed. ) Advances in Enzyme Regulation, pp. 27–55, New York: Pergamon Press, 1983). The IC$_{50}$ of MMS was 0.82 mM in SW480 and 1.4 mM in HCT116 cells. This difference is smaller that the difference in the TMZ IC$_{50}$ between these cell lines, probably because the low level of O$^6$mG adducts formed by MMS increases the impact of other DNA adducts. After cells were treated with MMS (0–3 mM) plus 6 mM MX for 1 hr, the IC$_{50}$ DMFs, compared to MMS alone, were 2.0 in SW480 and 2.3 in HCT116 (FIG. 2: A. HCT116 cells; B. SW480 cells. (■), MMS alone; (♦), MX plus MMS; (●), BG plus MMS; (▲), BG and MX plus MMS). These DMFs were similar to that observed with TMZ/Compared to treatment of SW480 with BG plus TMZ (DMF was 14), BG plus MMS induced less enhancement of cytotoxicity (DMF was 6). When MMS was combined with BG and MX, >10 fold potentiation of cytotoxicity was observed SW480, whereas, no additive effect was seen in HCT116 cells. In SW480 cells, the increased MMS-toxicity by BG suggests that even the small number of O$^6$mG adducts, they contribute to cytotoxicity. In HCT116 cells, increased cytotoxicity was only observed in the combination of TMZ with MX but not with BG, indicating that MX interfered with processing of N$^7$mG and N$^3$mA lesions which killed cells. From there data, we infer that MX had equal ability to interrupt BER in theses two cell lines.

EXAMPLE 2
Inhibitors of PARP Modulate the Sensitivity of Cells to TMZ

Since inhibitors of PARP may interrupt BER and increase sensitivity to methylating agents, we examined whether inhibitors of PARP sensitize cells to TMZ. FIG. 3a and FIG. 4a ((■), TMZ alone; (♦), BG plus TMZ; (●), PD128763 plus TMZ; (▲), BG and TMZ plus PD128763) display survival after combined treatment of TMZ with PD128763, 3-AB or 6-AN in both SW480 and, HCT116 cells. In the SW480 cell line, PD128763 sensitized cells to TMZ with a DMF of 3.3 fold. The combination of PD128763, BG TMZ was even more toxic, with a DMF compared to TMZ alone of 36-fold. In HCT116 cells, the DMF for PD128763 and TMZ compared to TMZ alone was 5.0. However, the combination of PD128763, BG and TMZ had no greater effect than PD128763 and TMZ, indicating that persistent O$^6$mG had no effect on cytotoxicity in this MMR defective cell line. Potentiation of TMZ cytotoxicity was also observed in both cell lines treated with two other PARP inhibitors, 3-AB (FIG. 3b, 4b: (■), TMZ alone; (♦), BG plus TMZ; (●), 6-AN plus TMZ; (▲), BG and TMZ plus 6-AN) and 6-AN (FIG. 4c, 4c: (■), TMZ alone; (♦), BG plus TMZ; (●), 3-AB plus TMZ; (▲), BG and TMZ plus 3-AB). Although the specific activity of these agents varied considerably, the DMFs were similar, 3–4-fold, for both 3-AB and 6-AN.

EXAMPLE 3
Synergistic Interaction Between TMZ and MX or PD128763

We investigated the nature of the reaction between TMZ and MX in the TMZ-resistant cell line, HCT116. These cells were incubated in the presence of a range of concentrations of TMZ (75–750 $\mu$M), of MX (1.5–15.0 mM), or constant molar ratio mixture of TMZ and MX (1:20) for 2 hr. HCT116 cells were also exposed to TMZ and PD128763 (62.5–625 $\mu$M) alone and to a combination of (1:0. 83) for 2 hr to analyze synergism. As shown in FIG. 5A and 5B, synergistic interaction (CI<<1, p<0.001) was found in both SW480 cells and, HCT116 cells using the combination of TMZ with either MX or PD128763. These results also showed a marked synergism at high Fa values. Since MDF for these combinations was similar to the observed with SW480 cells, we conclude that BER inhibitor synergizes methylating agent cytotoxicity in both MMR deficient and proficient colon cancer cells.

EXAMPLE 4
Effect of BER Inhibitors on BCNU Cytotoxicity

Figure 6B:
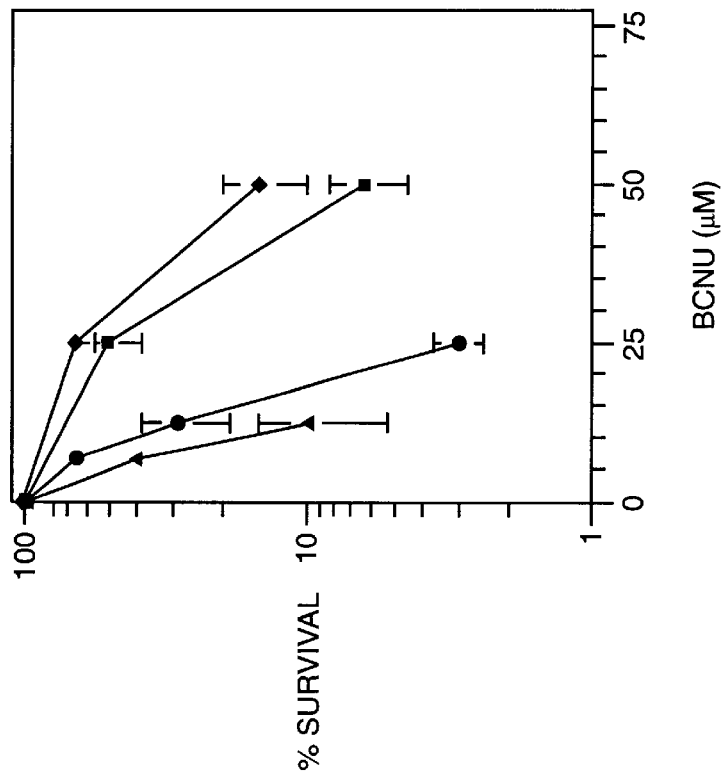
FIG. 6. Survival fraction of human colon cancer cell lines after exposure to BCNU plus MX. Cells were treated with 0–100 µM BCNU for 2 h or BCNU and 6 mM MX plus 10 µM BG for 2 h prior to 2 h exposure to BCNU. A. HCT116 cells; B. SW480 cells. (■), BCNU alone; (♦), MX plus BCNU; (●), BG plus BCNU; (▲), BG plus Mx plus BCNU. Results are the mean ±SD of at least three separate experiments performed in duplicate.
Figure 6A:
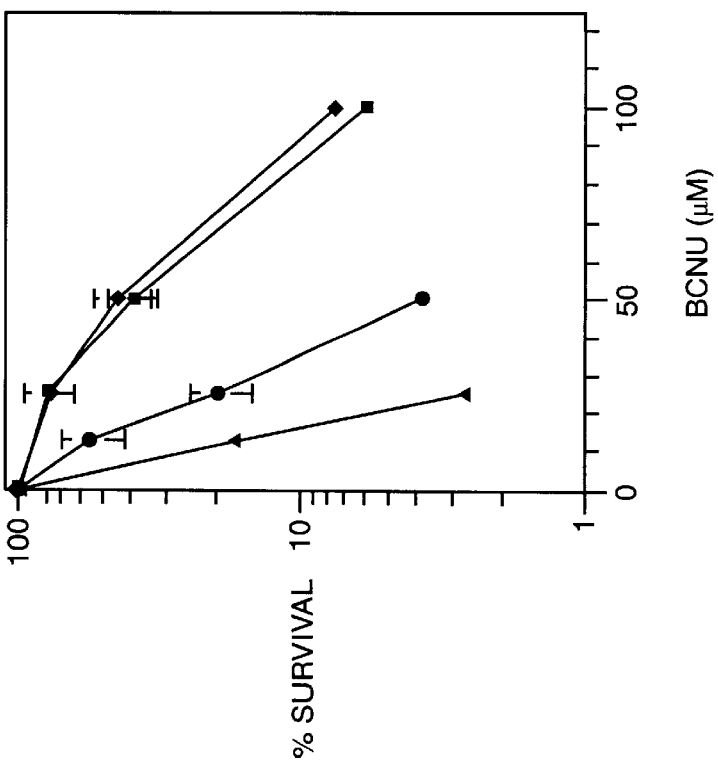
Figure 7B:
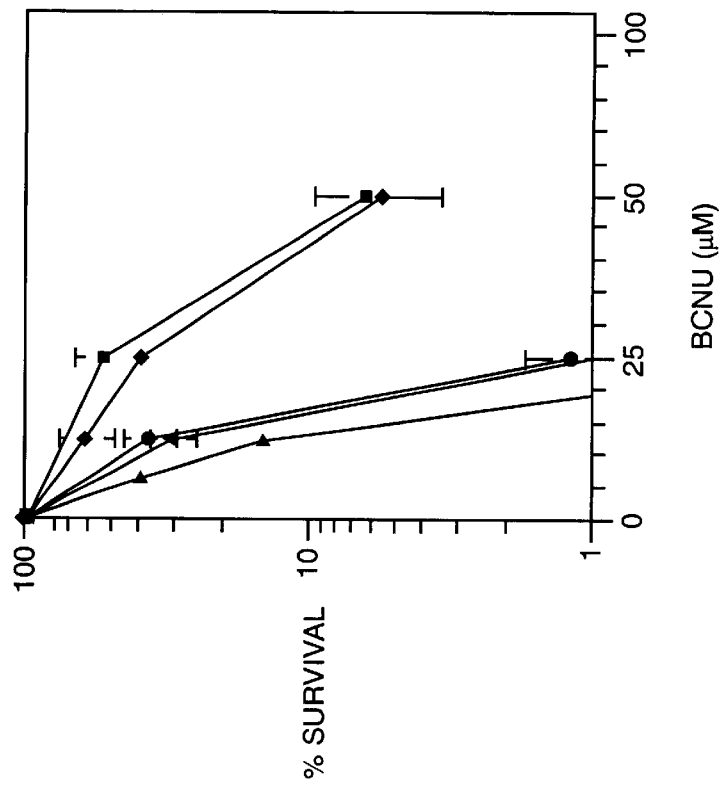
FIG. 7. Survival fraction of human colon cancer cell lines after exposure to BCNU plus PD128763. Cells were treated with 0–100 µM BCNU for 2 h or BCNU and 100 µM PD 128763 plus 10 µM BG for 2 h prior to 2 h exposure to BCNU. A. HCT116 cells; B. SW480 cells. (■), BNCU alone; (♦) PD128763 plus BCNU; (●), BG plus BCNU; (▲), BG and PD128763 plus BCNU; (▶), BG, PD128763 and MX plus BCNU. Results are the mean ±SD of at least three separate experiments performed in duplicate.
Figure 7A:
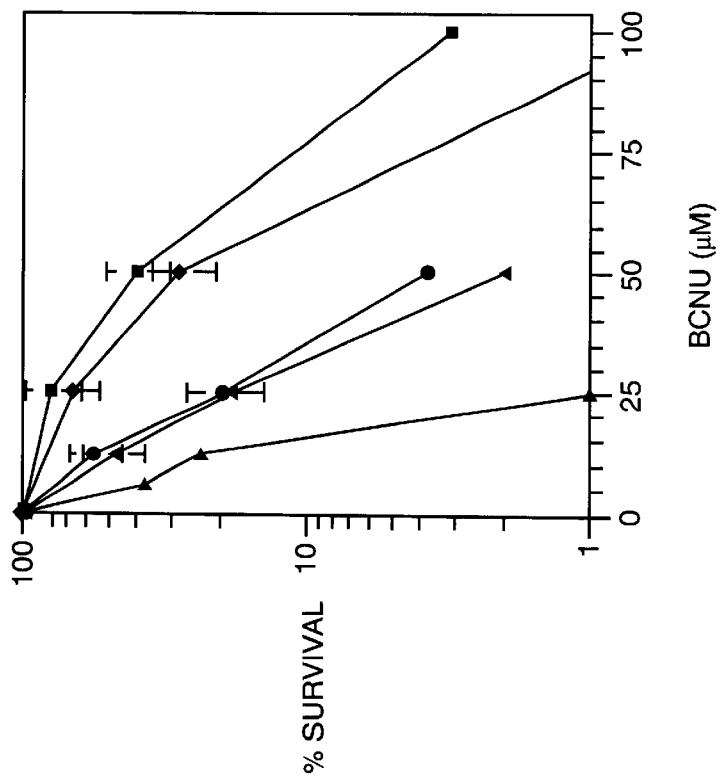

To test whether MX is also able to sensitize colon cancer cells to chloroethylating agents, these two cell lines were pretreated with 6 mM MX for 2 hr followed by BCNU. No enhancement of BCNU cytotoxicity by MX was observed (FIG. 6); the BCNU $IC_{50}$ was 45 µM in HCT116 cells (FIG. 6A: (■), BCNU alone; (♦), MX plus BCNU; (●), BG plus BCNU; (▲), BG plus MX plus BCNU) and 27–29 µM in SW480 cells, respectively, treated with BCNU alone or BCNU plus MX (FIG. 6B: (■), BCNU alone; (♦), MX plus BCNU; (●), BG plus BCNU; (▲), BG plus MX plus BCNU). A greater sensitization to BCNU was observed in these two cell lines when cells were treated with MX plus BG and BCNU, in which the BCNU $IC_{50}$ for both cell lines was 5 µM. However, most of the effect was potentiated due to BG, which increased BCNU cytotoxicity by 3–4 fold. As shown in FIG. 7, no sensitization to BCNU cytotoxicity was seen after treatment with PD128763 or BG and PD128763 ((■) by BNCU alone; (♦), PD128763 plus BCNU; (●), BG plus BCNU; (▲), BG and PD128763 plus BCNU; (▶), BG, PD128763 and MX plus BCNU).

EXAMPLE 5
Effect of Inhibitors of BER on Cell Cycle Distribution and PARP Cleavage The cell cycle and apoptosis response of SW480 and HCT116 cells was examined at various times after treatment with TMZ (300 µM) alone or with either MX (6 mM), PD128763 (100 µM) or BG (25 µM). After treatment, cells were divided into two aliquotes for analysis of cell cycle/apoptosis on days 1 and 3, and (see below) for detection of PARP cleavage. Cell cycle distribution was measured by flow cytometry according to DNA content and estimation of the duration of G1, S and G2/M was based on untreated, exponentially growing, asynchronous cells. MX and PD128763 alone did not affect the distribution of the cell cycle in these two cell lines (data not shown). At 24 hr, 75–90% of SW480 cells accumulated in S and G2 after treatment with TMZ alone and this G2/S phase arrest was more pronounce in cells pretreated with either MX or PD128763 S/G2 arrest was still present at 3 days in cells treated with the combination of MX or PD128763 and TMZ (in both instances, 13–20% of the cells were apoptotic). In SW480 cells treated with TMZ alone, the G2/S block was less obvious at day 3 with only 8% of the cells showing evidence of apoptosis. See, FIG. 8, panels A–J. In contrast, HCT116 cells had a normal cell cycle distribution after treatment with TMZ alone and no effect was seen with BG and TMZ. However, accumulation in S phase was observed 24 hr after treatment with PD128763 plus TMZ. At 72 hr, HCT116 cells had moved through S phase and thereafter, a significant portion of cells (90%) remained arrested in G2 with apoptosis present in 1% of the cells. A similar but less striking result was observed with MX and TMZ in HCT116 cells. By 72 hr, 60% of cells were still arrested in S and G2 and 10% of the cells were apoptotic. See, FIG. 8, panels K–T.

Figure 9:
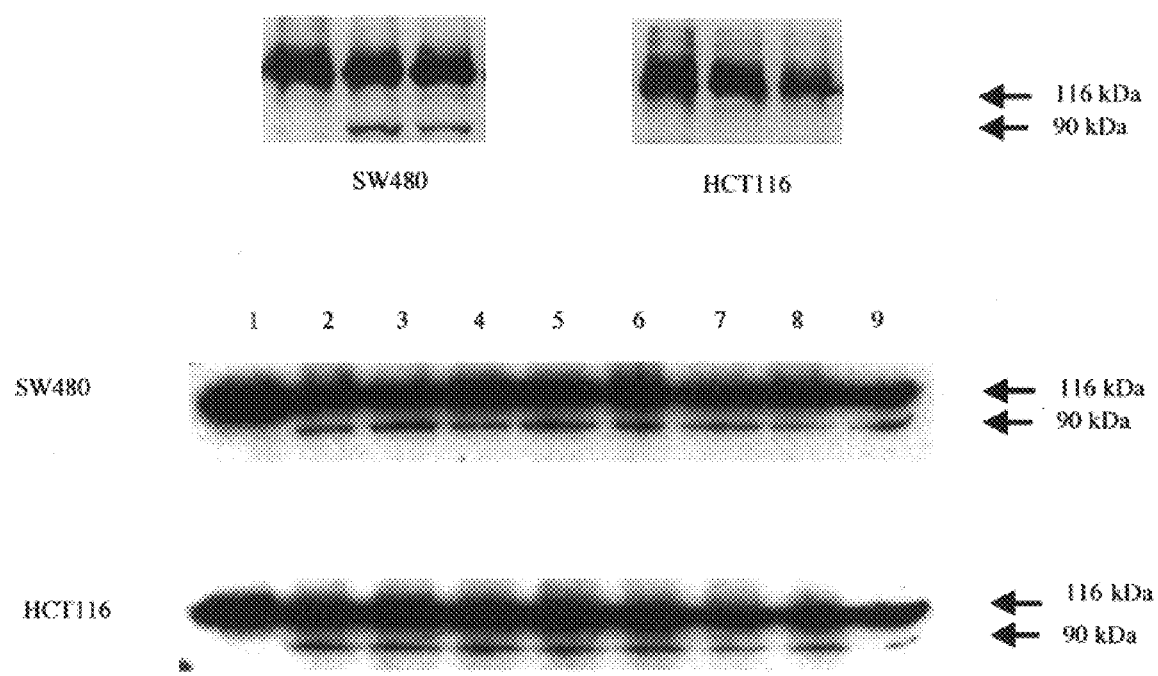
FIG. 9. PARP cleavage in colon cancer cells treated with TMZ plus modifiers. A. Controls, as labeled. B. SW480 cells; C. HCT116 cells; Lane 1, untreated; 2, TMX plus MX; 3, TMZ plus MX plus BG; 4, TMZ plus 3-AB; 5, TMZ plus 3-AB plus BG; 6, TMZ plus 6-AN; 7, TMZ plus 6-AN plus BG; 8, TMZ plus PD128763; 9, TMZ plus PD128763 plus BG.

Finally, as a marker of apoptosis induced cell death, we examined PARP cleavage after cells were treated with these drug combinations at 3 days (FIG. 9). PARP cleavage was observed in SW480 cells after exposure to TMZ alone and TMZ plus BG, but was not seen in HCT116 cells with the same treatment, indicating that the apoptotic precess is triggered when $O^6mG$ lesions are repaired by the MMR system. However, PARP cleavage was detected in MMR wild type and deficient cells treated wit TMZ plus either MX or PARP inhibitors.

EXAMPLE 6
Acute Toxicity of MX

Three mice per group were injected (i.p.) with MX at doses of 1, 2, 4, 6, 10 and 15 mg/kg for the test of acute toxicity. MX was lethal at 15 mg/kg causing death within 10 mins. At 10 mg/kg, mice appeared to have decreased motility but recovered one hour after treatment. Lower doses did not appear toxic.

Figure 10:
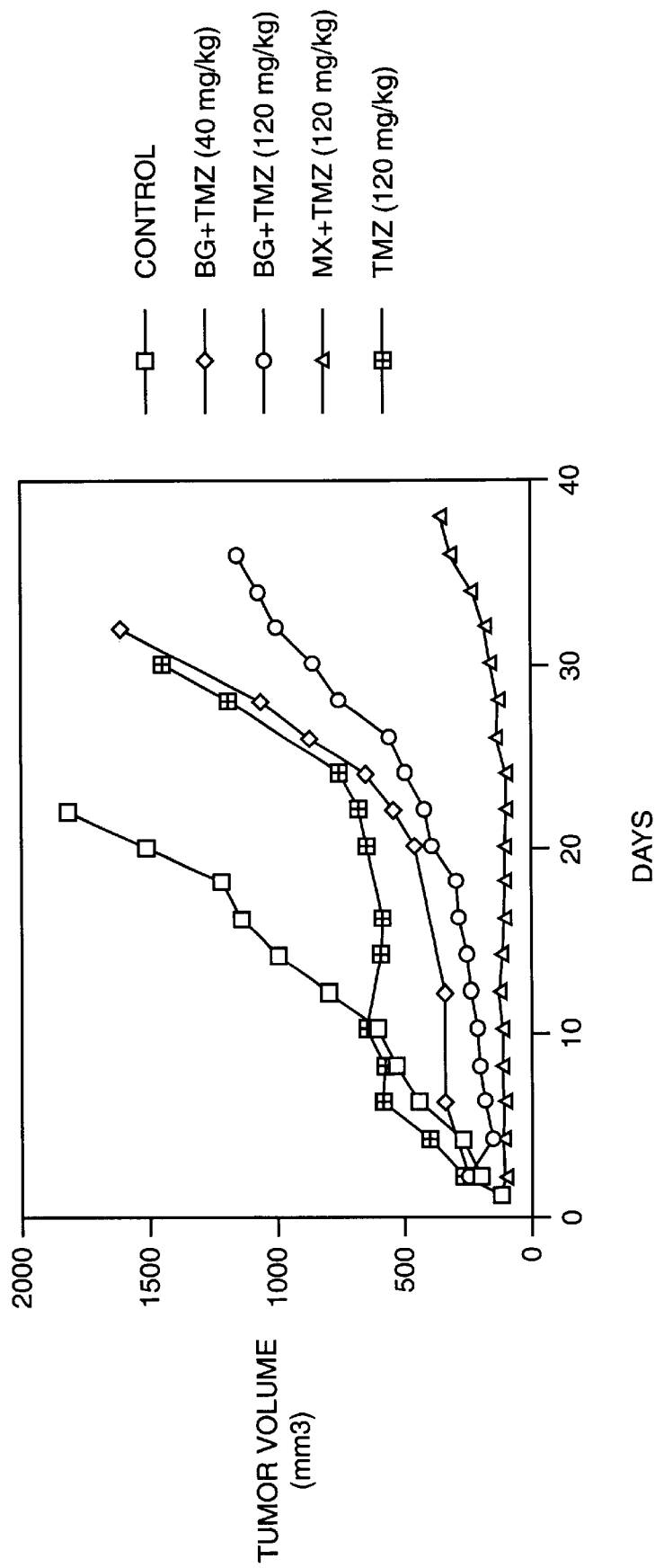
FIG. 10. The effect of MX plus TMZ on growth of SW480 xenograft.

EXAMPLE 7
Antitumor Effect of TMZ or TMZ combined with either BG or MX on SW480 Tumor Xenograft The response of SW480 xenograft to TMZ alone and combined treatments was shown in FIG. 10 and Table 1. At the highest tolerable does of TMZ, 120 mg/kg, a tumor growth delay of approximately 12 days was noted, indicating that SW480 is sensitive to TMZ. When given 30 mg/kg of BG for one hour prior to 40 mg/kg of TMZ, tumor growth delay was enhanced by BG up to 3-fold. Slightly greater efficacy was seen by combining the BG with high doses of TMZ, but significant weight loss (maximum body weight loss from 26 to 20 g, 23%) and very low leukocyte counts (90% decreased) at day 5 after the last treatment were observed in the mice. In contrast mice treated with 0.2 mg/kg MX plus 120 mg/kg TMZ had an immediate cessation of tumor growth for 20 days and very slow regrowth of the tumor with tumor growth delays over 40 days (p<0.02). There was no evidence of toxicity to mice with this combined treatment.

Figure 11:
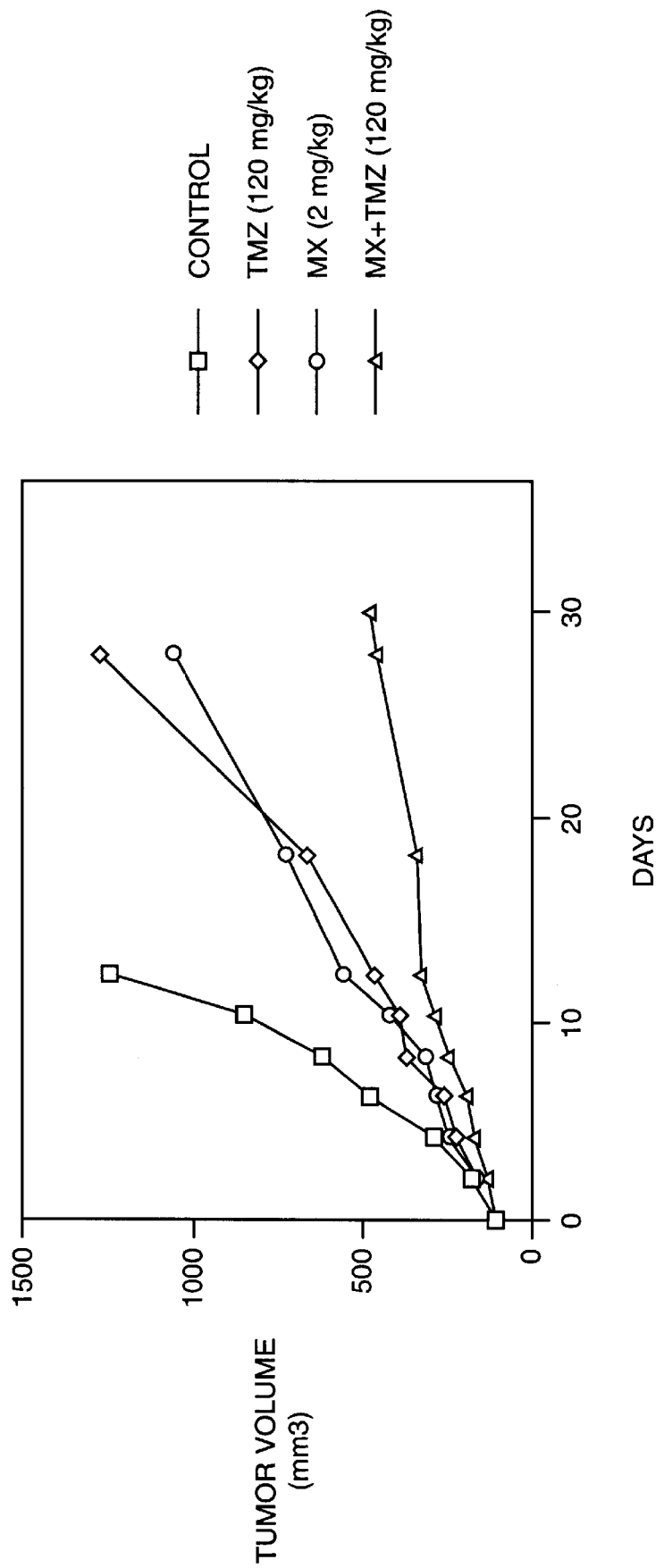
FIG. 11. The effect of MX plus TMZ on growth of HCT116 xenograft.

EXAMPLE 8
Antitumor Effect of TMZ or TMZ Combined with MX on HCT116 Tumor Xenograft Mice bearing HCT116 xenograft appeared to be relatively sensitive to all treatment. Body weight loss was observed in all treated groups (Table 2). BG plus TMZ caused 28% body weight loss and toxic death (2 of 5 mice) at 5 days after treatment. As shown in FIG. 11, HCT116 xenografts treated either with TMZ or MX alone had similar growth rate and growth delays of tumor treated with 0.5 mg/kg MX plus 120 mg/kg TMZ were significantly prolonged compared with control tumors (p<0.05).

These experiments demonstrate that a significant enhancement of antitumor effect of TMZ by MX or PARP inhibitors in human colon cancer xenographs with mismatch repair proficiency and deficiency. Therefore, from the above it should be clear that the present invention provides a wide variety of ways to 1) screen for compounds that can potentiate TMZ treatment of cancer, 2) provide model systems for the study of cancer treatment by agents that modulate DNA repair mechanisms and, 3) provide treatments for various cancers.

TABLE 1

SW480 xenograft toxicity and tumor response

| Group | Doses (mg/kg) | Toxicity (max. BW loss) | Tumor growth delays (Days) |
|---|---|---|---|
| TMZ | 120 | 11% (27 ± 1.9 – 24 ± 2.4 g) | 9.3 ± 1.2 |
| MX | 2 | 0% | 2.0 ± 0.5 |

TABLE 1-continued

SW480 xenograft toxicity and tumor response

| Group | Doses (mg/kg) | Toxicity (max. BW loss) | Tumor growth delays (Days) |
|---|---|---|---|
| BG + TMZ | 30/120 | 23% (26 ± 1.5 – 20 ± 0.5 g) | 10.3 ± 2.4 |
| MX + TMZ | 2/120 | 8% (26 ± 1.5 – 24 ± 1.5 g) | 27.0 ± 1.2 |

TABLE 2

HCT116 xenograft toxicity and tumor response

| Group | Doses (mg/kg) | Toxicity (max. BW loss) | Tumor growth delays (Days) |
|---|---|---|---|
| TMZ | 120 | 20.8% (24 ± 1.3 – 19 ± 1.7 g) | 2.5 ± 0.8 |
| MX | 2 | 8.3% (24 ± 1.6 – 22 ± 1.4 g) | 2.2 ± 0.4 |
| BG + TMZ | 30/120 | 28.0% (25 ± 0.8 – 18 ± 0.5 g)* | NA |
| MX + TMZ | 2/120 | 19.2% (26 ± 1.3 – 21 ± 0.4 g) | 17.0 ± 1.2 |

*toxic death: 2/5 mice
NA, did not analyze

What is claimed is:

1. A method comprising:
   a) providing i) a patient diagnosed with cancer, ii) a first formulation comprising methoxyamine and iii) a second formulation comprising temozolomide;
   b) administering said first formulation to said patient; and
   c) administering said second formulation to said patient wherein methoxyamine is administered in an amount sufficient to potentiate toxicity of temozolomide.

2. The method of claim 1, wherein said methoxyamine and said temozolomide are administered sequentially.

3. The method of claim 1, wherein said methoxyamine and said temozolomide are administered as a formulation.

4. The method of claim 1, wherein said methoxyamine and said temozolomide are administered orally.

5. The method of claim 1, wherein said methoxyamine and said temozolomide are administered intravenously.

6. The method of claim 1, wherein said methoxyamine is administered in an amount effective to inhibit apurinic/apyrimidinic endonuclease, and said temozolomide is administered in a dose of between 0.1 and 200 mg/kg body weight per day.

7. The method of claim 6, wherein said dose of temozolomide is between 1 and 20 mg/kg body weight per day.

8. The method of claim 1, wherein said amount of methoxyamine is an amount sufficient to sensitize the cancer without causing undue sensitization of normal tissue.

9. A method comprising:
   a) providing i) a patient diagnosed with cancer, wherein said cancer is resistant to treatment by temozolomide alone, ii) a first formulation comprising methoxyamine and iii) a second formulation comprising temozolomide;
   b) administering said first formulation to said patient; and
   c) administering said second formulation to said patient wherein methoxyamine is administered in an amount sufficient to potentiate toxicity of temozolomide.

10. The method of claim 9, wherein said methoxyamine and said temozolomide are administered sequentially.

11. The method of claim 9, wherein said methoxyamine and said temozolomide are administered as a formulation.

12. The method of claim 9, wherein said-methoxyamine is administered in an amount effective to inhibit apurinic/apyrimidinic endonuclease, and said temozolomide is administered in a dose of between 0.1 and 200 mg/kg body weight per day.

13. The method of claim 12, wherein said dose of temozolomide is between 1 and 20 mg/kg body weight per day.

14. The method of claim 12, wherein said amount of methoxyamine is an amount sufficient to sensitize the cancer without causing undue sensitization of normal tissue.

15. A method comprising:
   a) providing i) a patient diagnosed with cancer, wherein said cancer is selected from the group consisting of carcinomas, melanomas, sarcomas, lymphomas, leukemias, astrocytomas, gliomas, malignant melanomas, chronic lymphocytic leukemia, lung cancers, and breast cancers, and wherein said cancer is resistant to treatment with temozolomide alone, ii) a first formulation comprising methoxyamine and iii) a second formulation comprising temozolomide;
   b) administering said first formulation to said patient; and
   c) administering said second formulation to said patient wherein methoxyamine is administered in an amount sufficient to potentiate toxicity of temozolomide.

16. The method of claim 15, wherein said methoxyamine and said temozolomide are administered sequentially.

17. The method of claim 15, wherein said methoxyamine and said temozolomide are administered as a formulation.

18. The method of claim 15, wherein said methoxyamine is administered in an amount effective to inhibit apurinic/apyrimidinic endonuclease, and said temozolomide is administered in a dose of between 0.1 and 200 mg/kg body weight per day.

19. The method of claim 18, wherein said dose of temozolomide is between 1 and 20 mg/kg body weight per day.

20. The method of claim 18, wherein said amount of methoxyamine is an amount sufficient to sensitize the cancer without causing undue sensitization of normal tissue.

21. A formulation comprising methoxyamine and temozolomide wherein methoxyamine is administered in an amount sufficient to potentiate toxicity of temozolomide.

* * * * *